(12) United States Patent
Hediger

(10) Patent No.: US 7,371,536 B2
(45) Date of Patent: May 13, 2008

(54) METHODS FOR TRANSPORTING VITAMIN C

(76) Inventor: Matthias A. Hediger, 74 Edmunds Rd., Wellesley, MA (US) 02481

( * ) Notice: Subject to any disclaimer, the term of this patent is extended or adjusted under 35 U.S.C. 154(b) by 344 days.

(21) Appl. No.: 10/408,713

(22) Filed: Apr. 7, 2003

(65) Prior Publication Data

US 2004/0006019 A1    Jan. 8, 2004

Related U.S. Application Data

(62) Division of application No. 09/551,421, filed on Apr. 18, 2000, now abandoned.

(60) Provisional application No. 60/164,163, filed on Nov. 8, 1999.

(51) Int. Cl.
*G01N 33/53* (2006.01)
(52) U.S. Cl. ........................................ 435/7.2; 435/325
(58) Field of Classification Search ...................... None
See application file for complete search history.

(56) References Cited

U.S. PATENT DOCUMENTS 5,858,707 A    1/1999 Guimaraes et al. ........ 435/69.1

OTHER PUBLICATIONS

Faaland et al. (1998) "Molecular Characterization of Two Novel Transporters From Human and Mouse Kidney and From LLC-PK1 Cells Reveals a Novel Conserved Family that is Homologous to Bacterial and *Aspergillus* Nucleobase Transporters", Biochimica et Biophysica Acta, 1442:353-360.
Tsukaguchi et al. (1999) "A Family of Mammalian $Na^+$- Dependent L-Ascorbic Acid Transporters", Nature, 399:70-75.
Daruwalas et al. (1999) "Cloning and Functional Characterization of the Human Sodium-dependent Vitamin C Transporters hSVCT1 and hSVCT2", FEBS Letter, 460:480-484.

*Primary Examiner*—Michael Pak
(74) *Attorney, Agent, or Firm*—Goodwin Procter LLP

(57) ABSTRACT

The invention provides methods for regulating the transport of vitamin C across membranes.

7 Claims, 20 Drawing Sheets

```
hSVCT1   ----------  ----------  ----------  ----------  ----------
rSVCT1   ----------  ----------  ----------  ----------  ----------
mSVCT1   ----------  ----------  ----------  ----------  ----------
hSVCT2   MMGIGKNTTS  KSMEAGSSTE  GKYEDEAKHP  AFFTLPVVIN  GGATSSGEQD
rSVCT2   MMGVGKNT.S  KSVEVGGSTE  GKYEEEAKRP  DFFTLPVVIN  GGATSSGEQD
pSVCT2   MMGIGK.TSS  KSMEAGSSAE  GKYEDEAKHP  TFFTLPVVTN  GGATSSGEQD
         1 hSVCT1   LCILLGFQHY  LTCFSGTIAV  PFLLAEALCV  GHDQHMVSQL  IGTIFTCVGI
rSVCT1   LCILLGFQHY  LTCFSGTIAV  PFLLAEALCV  GRDQHMISQL  IGTIFTCVGI
mSVCT1   LCIFLGFQHY  LTCFSGTIAV  PFLLAEALCV  GRDQHMVSQL  IGTIFTCVGI
hSVCT2   LCIFLGLQHY  LTCFSGTIAV  PFLLADAMCV  GYDQWATSQL  IGTIFFCVGI
rSVCT2   LCIFLGLQHY  LTCFSGTIAV  PFLLADAMCV  GDDQWATSQL  IGTIFFCVGI
pSVCT2   LCIFLGLQHY  LTCFSGTIAV  PFLLADAMCV  GYDQWATSQL  IGTILFCVGI
         101                                                     2
```

| FIG. 1A | FIG. 1B |
|---|---|
| FIG. 1C | FIG. 1D |
| FIG. 1E | FIG. 1F |
| FIG. 1G | |

```
                                                                    100
-MRAQEDLEG RTQHE..... ..TRDPSTP LPTEPKFDML YKIEDVPPWY
-MKAQEDPGS SKQHECPDSA GTSTRDQQAP LPAEPKFDML YKIEDVPPWY
-MKTPEDPGS PKQHEVVDSA GTSTRDRQAP LPTEPKFDML YKIEDVPPWY
NEDTELMAIY TTENGIAEKS SLAETLDSTG SLDPQRSDMI YTIEDVPPWY
NEDTELMAIY TTENGIAEKS SLAETLDSTG SLDPQRSDMI YTIEDVPPWY
NEDTELMAIY TTENGIAEKS SLAETLDSTG SLDPQRSDMI YTIEDVPPWY
          *

200
TTLIQTTVGI RLPLFQASAF AFLVPAKAIL ALERWKCPPE EEIYGNWSLP
TTLIQTTVGI RLPLFQASAF AFLVPAKAIL ALERWKCPPE EEIYGNWSMP
TTLIQTTVGI RLPLFQASAF AFLVPAKSIL ALERWKCPSE EEIYGNWSMP
TTLIQTTFGC RLPLFQTSAF AFLAPARAIL SLDKWKCNTT DVSVANGTAE
TTLIQTTFGC RLPLFQASAF AFLAPARAIL SLDKWKCNTT EITVANGTAE
TTLIQTTFGC RLPLFQASAF AFLAPARAIL SLDKWKCNTT DVSVANGTTE
                     3

FIG. 1B
```

|       |     |        |       |       |      |       |       |       |       |
|-------|-----|--------|-------|-------|------|-------|-------|-------|-------|
| hSVCT1 | 201 | .LNTSH | IWHP | RIRE | VQGAIM | VSSVV | EVVIG | LLGLPGALLN | YIGPLTVTPT |
| rSVCT1 |     | .LNTSH | IWHP | RIRE | VQGAIM | VSSVV | EVVIG | LLGLPGALLS | YIGPLTVTPT |
| mSVCT1 |     | .LNTSH | IWHP | RIRE | VQGAIM | VSSMV | EVVIG | LMGLPGALLS | YIGPLTVTPT |
| hSVCT2 |     | LLHTEH | IWYP | RIRE | IQGAII | MSSLI | EVVIG | LLGLPGALLK | YIGPLTITPT |
| rSVCT2 |     | LL..EH | IWHP | RIQE | IQGAII | MSSLI | EVVIG | LLGLPGALLR | YIGPLTITPT |
| pSVCT2 |     | LLHTEH | MWYP | RIRE | IQGAII | MSSLI | EVVIG | LLGLPGALLK | YIGPLGITPT |

4

| | | | | | | | | |
|---|---|---|---|---|---|---|---|---|
| hSVCT1 | 301 | KGLTLLRIQI | FKMFPIMLAI | MTVWLLCYVL | TLTDVLPTDP | KAYGFQARTD |
| rSVCT1 |     | KGLTLFRIQI | FKMFPIVLAI | MTVWLLCYVL | TLTDVLPADP | TVYGFQARTD |
| mSVCT1 |     | KGLTLFRVQI | FKMFPIVLAI | MTVWLLCYVL | TLTDVLPADP | TVYGFQARTD |
| hSVCT2 |     | KGWTAYKLQL | FKMFPIILAI | LVSWLLCFIF | TVTDVFPPDS | TKYGFYARTD |
| rSVCT2 |     | KGWTAYKLQL | FKMFPIILAI | LVSWLLCFIF | TVTDVFPSNS | TDYGYYARTD |
| pSVCT2 |     | KGWTAYKLQL | FKMFPIILAI | LVSWLLCFIF | TVTDVFPPDS | TKYGFYARTD |

|     |     |     |     |     |     |     |     | 300 |     |     |
| --- | --- | --- | --- | --- | --- | --- | --- | --- | --- | --- |
| VSLIGLSVFQ | AAGDRAGSHW | GISACSILLI | ILFSQYLRNL | TFLLPVYRWG |
| VSLIGLSVFQ | AAGDRAGSHW | GISACSILLI | VLFSQYLRNL | TFLLPVYRWG |
| VSLIGLYVFQ | AAGDRAGSHW | GISACSILLI | VLFSQYLRNL | TFLLPVYRWG |
| VALIGLSGFQ | AAGERAGKHW | GIAMLTIFLV | LLFSQYARNV | KFPLPIYKSK |
| VALIGLSGFQ | AAGERAGKHW | GIAMLTIFLV | LLFSQYARNV | KFPLPIYKSK |
| VALIGLSGFQ | AAGERAGKHW | GIAMLTIFLL | LLFSQYARNV | KFPLPIYKSK |

▼  ▼▼
_____5_____

|     |     |     |     |     | 400 |
| --- | --- | --- | --- | --- | --- |
| ARGDIMAIAP | WIRIPYPCQW | GLPTVTAAAV | LGMFSATLAG | IIESIGDYYA |
| ARGDIMAISP | WIRIPYPCQW | GLPTVTVAAV | LGMFSATLAG | IIESIGDYYA |
| ARGDIMAISP | WIRIPYPCQW | GLPTVTVAAV | LGMFSATLAG | IIESIGDYYA |
| ARQGVLLVAP | WFKVPYPFQW | GLPTVSAAGV | IGMLSAVVAS | IIESIGDYYA |
| ARKGVLLVAP | WFKVPYPFQW | GMPTVSAAGV | IGMLSAVVAS | IIESIGDYYA |
| ARQGVLLVAP | WFKVPYPFQW | GLPTVSAAGV | IGMLSAVVAS | IIESIGDYYA |

|  | 401 | | | | | | |
|---|---|---|---|---|---|---|---|
| hSVCT1 | CARLAGAPPP | PVHAINRGIF | TEGICCIIAG | LLGTGNGSTS | SSPNIGVLGI |
| rSVCT1 | CARLAGAPPP | PVHAINRGIF | TEGVCCIIAG | LLGTGNGSTS | SSPNIGVLGI |
| mSVCT1 | CARLAGAPPP | PVHAINRGIF | TEGICCIIAG | LLGTGNGSTS | SSPNIGVLGI |
| hSVCT2 | CARLSCAPPP | PIHAINRGIF | VEGLSCVLDG | IFGTGNGSTS | SSPNIGVLGI |
| rSVCT2 | CARLSCAPPP | PIHAINRGIF | VEGLSCVLDG | VFGTGNGSTS | SSPNIGVLGI |
| pSVCT2 | CARLSCAPPP | PIHAINRGIF | VEGLSCVLDG | IFGTGNGSTS | SSPNIGVLGI |

8

|  | 501 | | * | | | | | | | * | |
|---|---|---|---|---|---|---|---|---|---|---|---|
| hSVCT1 | VGLSNLQFVD | MNSSRNLFVL | GFSMFFGLTL | PNYLESNPGA | INTGILEVDQ |
| rSVCT1 | VGLSNLQFVD | MNSSRNLFVL | GFSMFFGLTL | PNYLDSNPGA | INTGVPEVDQ |
| mSVCT1 | VGLSNLQFVD | MNSSRNLFVL | GFSMFFGLTL | PNYLDSNPGA | INTGIPEVDQ |
| hSVCT2 | VGLSNLQFID | LNSSRNLFVL | GFSIFFGLVL | PSYLRQNP.. | LVTGITGIDQ |
| rSVCT2 | VGLSNLQFID | LNSSRNLFVL | GFSIFFGLVL | PSYLRQNP.. | LVTGITGIDQ |
| pSVCT2 | VGLSNLQFID | LNSSRNLFVL | GFSIFFGLVL | PSYLRQNP.. | LVTGITGVDQ |

```
                                                          500
TKVGSRRVVQ YGAAIMLVLG TIGKFTALFA SLPDPILGGM FCTLFGMITA
TKVGSRRVVQ YGAGIMLILG AIGKFTALFA SLPDPILGGM FCTLFGMITA
TKVGSRRVVQ YGAGIMLILG AIGKFTALFA SLPDPILGGM FCTLFGMITA
TKVGSRRVIQ CGAALMLALG MIGKFSALFA SLPDPVLGAL FCTLFGMITA
TKVGSRRVIQ YGAALMLGLG MIGKFSALFA SLPDPVLGAL FCTLFGMITA
TKVGSRRVIQ YGAASCCALG MIGKFSALFA SLPDPVLGAL FCTLFGMITA
*                               *
                   9                  10

* 600
ILIVLLTTEM FVGGCLAFIL DNTVPGSPEE RGLIQWKAGA HANSDMSSL
ILTVLLTTEM FVGGCLAFIL DNTVPGSPEE RGLIQWKAGA HANSETLASL
ILTVLLTTEM FVGGCLAFIL DNTVPGSPEE RGLIQWKAGA HANSETSASL
VLNVLLTTAM FVGGCVAFIL DNTIPGTPEE RGIRKWKKGV GKGNKSLDGM
VLNVLLTTAM FVGGCVAFIL DNTIPGTPEE RGIRKWKKGV SKGNKSLDGM
VLNVLLTTAM FVGGCVAFIL DNTIPGTPEE RGIRKWKKGV GKGCKSLDGM
            12
```

FIG. 1F

METHODS FOR TRANSPORTING VITAMIN C

RELATED APPLICATIONS

This application claims the benefits of U.S. application Ser. No. 09/551,421, filed on Apr. 18, 2000, now abandoned which claims priority to U.S. Provisional Application Ser. No. 60/164,163, filed on Nov. 8, 1999, the entirety of which are hereby incorporated by reference.

BACKGROUND OF THE INVENTION

1. Field of the Invention

The present invention relates to transcellular transport or cellular uptake of vitamin C (L-ascorbate), and in particular to compositions encoding transport proteins for vitamin C and methods for its preparation and use.

2. Background Information

Vitamin C is an essential multi-functional micronutrient required in its reduced form (L-ascorbic acid) for many enzymatic reactions and as a scavenger of free radicals generated from numerous physiological and pathological processes. It has been known for more than 70 years that vitamin C is essential to the human body, and the disease scurvy, caused by an extreme deficiency of vitamin C, has been known for hundreds of years. But surprisingly, little has heretofore been discovered about how the body actually absorbs vitamin C, and how the vitamin is distributed to the many organs at appropriate concentrations to ensure crucial enzymatic reactions (e.g., collagen synthesis) and to protect tissues and organs from oxidative damage.

Several facilitative hexose transporters (of the GLUT family) are known to transport dehydroascorbic acid (but not L-ascorbic acid) in vitro. Although the oxidized form of the vitamin has the same oral bioactivity as L-ascorbic acid, the GLUT-type transporters are unlikely to account for significant absorption of the vitamin as long as glucose is present in the lumen. Whereas several human cell types have been shown to possess high capacity dehydroascorbic acid transport activity in vitro, these systems may have only limited physiological significance because vitamin C is present in human plasma essentially only in its reduced form, so the GLUT systems would not be expected to participate in the cellular uptake of the vitamin. The exception is in the "recycling" of the oxidized vitamin, e.g., in activated neutrophils or erythrocytes, under conditions in which the extracellular dehydroascorbic acid concentration may be locally high.

There are numerous suggestions in the literature regarding the involvement of vitamin C in a variety of human diseases. Studies indicate that vitamin C levels are reduced in the elderly, smokers, and cancer patients, and that defective serum antioxidant status contributes to the increased oxidative stress associated with many diseases. For example, oxidative stress in the central nervous system (CNS) may cause oxidation of lipoprotein, which can itself initiate the neuronal cell death leading to the manifestation of neurodegenerative diseases. Epidemiological research suggests that dietary vitamin C supplementation is effective in the prevention of various types of cancer, including bladder, breast, cervical, colorectal, esophageal, lung, pancreatic, prostate, salivary gland, stomach, leukemia, and non-Hodgkin's lymphoma. Vitamin C may also play a protective role in atherogenesis, since epidemiological studies indicate that plasma ascorbic acid levels are inversely related to mortality due to coronary heart disease.

DESCRIPTION OF THE INVENTION

Brief Summary of the Invention

One aspect of the invention comprises, as a composition of matter, a non-naturally occurring vitamin C-transporter protein. The transporter protein is found to exist in two forms, referred to herein as SVCT1 and SVCT2. Localization studies demonstrate that SVCT1 is largely confined to bulk-transporting epithelia such as intestine and kidney, where it serves whole-body homeostasis. SVCT2 appears to account for the widespread tissue-specific uptake of vitamin C, and is found in neural, endocrine, exocrine and endothelial tissues as well as in osteoblasts. In the eye, SVCT2 likely transports vitamin C into the aqueous humor, the cornea and the lens (where the vitamin is required at high concentration for protection against UV radiation and oxidative stress). On the other hand, excessive vitamin C accumulation may promote the growth of astrocytic brain tumors (gliomas).

The cloning of these transporters facilitates understanding of how they function to regulate an appropriate supply of the vitamin in various tissues and the role they play in protection against oxidative stress. This advance also facilitates identification of therapeutic opportunities involving vitamin C (e.g., for protection against viral infections (such as the common cold), cataract, and certain types of cancer and leukemias).

Preferably, the transporter is a polypeptide encoded by a nucleic acid sequence within SEQ ID NO: 1, 3, 5, or 6. In this context, the term "encoded" refers to an amino-acid sequence whose order is derived from the sequence of the nucleic acid or its complement. The nucleic acid sequences represented by SEQ ID NOS:1 and 2 are derived from human sources. The nucleic acid sequences represented by SEQ ID NOS: 5 and 6 are derived from rat.

Accordingly, one embodiment of this aspect of the invention is directed toward an isolated transporter having an amino-acid sequence substantially corresponding at least to the conserved regions of SEQ ID NO: 3, 4, 7 or 8. The term "substantially," in this context, refers to a polypeptide that may comprise substitutions and modifications that do not alter the physiological activity of the protein to transport calcium across cellular membranes. The polypeptide represented by SEQ ID NO: 2 is derived from human sources. The peptide represented by SEQ ID NO: 4 is derived from rat. The protein does not retain functionality as a free species. Thus, by "isolated" is meant integral with a cellular membrane or other lipid bilayer, or stabilized by an appropriate detergent (e.g., TRITON X-100, a surfactant available from Rohm & Haas, Philadelphia, Pa.).

In a second aspect, the invention pertains to a non-naturally occurring nucleic acid sequence encoding a vitamin C-transporter protein. One embodiment of this aspect of the invention is directed toward a transporter having a nucleotide sequence substantially corresponding at least to the conserved regions of SEQ ID NO: 1, 2, 5, or 6. The term "substantially," in this context, refers to a nucleic acid that may comprise substitutions and modifications that do not alter encoding of the amino-acid sequence, or which encodes a polypeptide having the same physiological activity in transporting vitamin C across cellular membranes. The term "corresponding" means homologous or complementary to a particular nucleic-acid sequence.

A third aspect of the invention comprises methods of using a membrane protein that functions to transport vitamin C across cellular membranes. One aspect of this embodiment of the invention comprises methods associated with a non-naturally occurring vitamin C-transporter protein. Once again, the transporter is preferably a polypeptide encoded by a nucleic acid sequence within SEQ ID NO: 1, 2, 5, or 6. Another aspect of this embodiment is directed toward uses of a transporter having an amino-acid sequence substantially corresponding at least to the conserved regions of SEQ ID NO: 3, 4, 7, or 8.

A fourth aspect of the present invention comprises a method of transporting vitamin C across a cellular membrane having a sodium-coupled protein transporter in accordance herewith. Vitamin C (as L-ascorbate or L-ascorbic acid is applied to the celluar membrane under conditions that facilitate its transmembrane penetration (cellular uptake) via the transporter.

In a fifth aspect, the invention comprises a method of identifying chemicals capable of interacting with the transporter, whether the protein is integral with a cellular membrane or other lipid bilayer, or stabilized by an appropriate detergent. Such chemicals may include antibodies or other targeting molecules that bind to the protein for purposes of identification, or which affect (e.g., by modulation or inhibition) the transport properties of the protein; products of combinatorial chemistry libraries; and transportable species other than vitamin C.

In a sixth aspect, the invention comprises a method of blocking or inhibiting or activating the uptake of vitamin C by cells having a transporter protein in accordance herewith. In one embodiment, the method comprises the steps of causing an antibody or other targeting molecule to bind to the protein in a manner that inhibits or activates vitamin C transport. In another embodiment, a nucleic acid complementary to at least a portion of the nucleic acid encoding the transporter protein is introduced into the cells. The complementary nucleic acid blocks or activates functional expression of the vitamin C transporter protein. In still another embodiment, an inhibitor such as phloretin is applied to the transporter.

In a seventh aspect, a drug is linked to a transported species in a cleavable manner. This facilitates oral administration of the drug, which is absorbed, with the transported species, into intestinal enterocytes. The drug is then cleaved from the transported species either within the cell or through hepatic metabolism (following its exit into the bloodstream).

SVCT1 and SVCT2 are each saturable, exhibiting high apparent affinity for L-ascorbic acid ($K_{0.5}$=50-100 μM), and $Na^+$-dependent. A coupling stoichiometry of 2 $Na^+$: 1 L-ascorbic acid for SVCT1 may be inferred based upon the following experimental observations: SVCT1-mediated L-ascorbic acid transport is both $Na^+$-dependent and electrogenic, generating inward currents (i.e., net inward positive-charge movements), despite transport of L-ascorbic acid in its deprotonated (1−) form (given the effective pH range of the transporter). This stoichiometry is further supported by the observation that two $Na^+$ ions are required to activate the transporter (from the Hill coefficient, based on voltage-clamp experiments).

SVCT1 is stereospecific and intensely favors L-ascorbic acid over D-isoascorbic acid, dehydroascorbic acid, L-ascorbic acid-2-phosphate and L-ascorbic acid-6-palmitate. SVCT1 transport activity is sensitive to changes in extracellular pH (optimum pH≈7.5), which may affect the binding affinity for L-ascorbic acid.

Human and rat SVCT1 and SVCT2 were found to be discretely distributed. SVCT1 had a limited distribution, mainly confined to the bulk transporting epithelia such as kidney and small intestine, but was also present in a few endocrine tissues, including a 9-kb transcript in human thymus. SVCT2 displayed a much broader distribution in brain, retina and spleen, and in several endocrine and neuroendocrine tissues. The possibility that SVCT1 and SVCT2 are localized to different cell types or to different membranes (apical or basolateral) within polarized epithelial cells has not been established. Alternatively, the fact that these two transporters share very similar functional characteristics yet remain discretely distributed may suggest that they are differentially regulated.

BRIEF DESCRIPTION OF THE DRAWINGS

The foregoing discussion will be understood more readily from the following detailed description of the invention, when taken in conjunction with the accompanying drawings, in which.

DETAILED DESCRIPTION OF THE PREFERRED EMBODIMENTS

1. SVCT1, SVCT2 and Their Nucleic Acids

With reference to SEQ ID NO: 1, a human-derived cDNA having a nucleotide sequence encoding SVCT1, a vitamin C-transport protein, contains 2306 nucleotides; an open reading frame of 1797 base pairs (bp) (i.e., nucleotides 48-1844) encodes the SVCT1 protein comprised of 598 amino acids, which is set forth as SEQ ID NO: 3. With reference to SEQ ID NO: 2, a human-derived cDNA having a nucleotide sequence encoding a SVCT2, a vitamin C-transport protein, contains 2010 nucleotides; an open reading frame of 1950 bp encodes a protein having 650 amino acids, which is set forth as SEQ ID NO: 4.

Figure 1G:
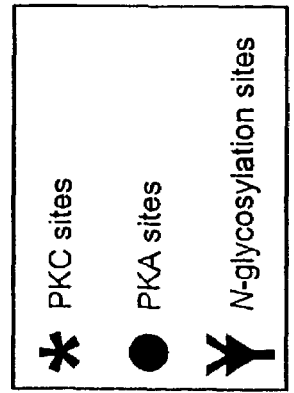
FIG. 1 illustrates the aligned amino acid sequences of human SVCT1 (SEQ ID NO: 3), rat SVCT1 (SEQ ID NO: 7), mouse SVCT1 (SEQ ID NO: 9), human SVCT2 (SEQ ID NO: 4), rat SVCT2 (SEQ ID NO: 8), and pig SVCT2 (SEQ ID NO: 10), with conserved residues shaded and the twelve putative transmembrane domains underlined and numbered.

SEQ ID NOS: 5 and 6 are rat-derived cDNA having nucleotide sequences encoding SVCT1 and SVCT2, respectively. Rat SVCT1 contains 2472 nucleotides, and an open reading frame of 1812 bp encodes the rat SVCT1 protein comprised of 604 amino acids, which is set forth as SEQ ID NO: 7. Rat SVCT2 contains 4001 nucleotides, and an open reading frame of 1776 bp encodes the rat SVCT1 protein comprised of 592 amino acids, which is set forth as SEQ ID NO: 8. Rat SVCT2 has 65% amino-acid identity to SVCT1. As illustrated in FIG. 1, the amino-acid sequences for each isoform (SVCT1 or SVCT2) showed over 90% identity across different species (human, rat, mouse, pig) and ≈65% identity between the SVCT1 and SVCT2 isoforms from different species. HSVCT 1 comprises 598 amino acid residues and is almost identical to a sequences designated YSPL3. SVCT1 and SVCT2 also show ≈34% sequence identity to the mouse yolk-sac permease-like (mYSPL1) protein of unknown function and ≈20-30% identity to putative nucleobase transporters in bacteria, yeast, and plants.

Figure 2:
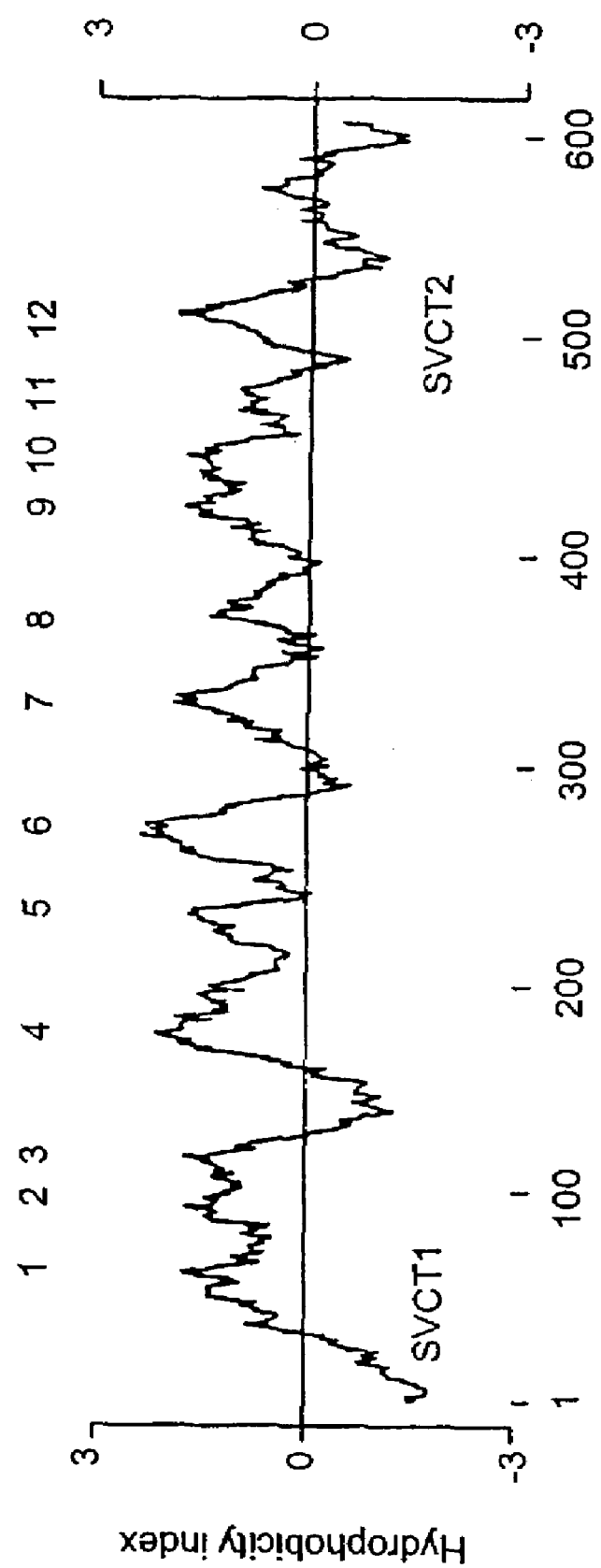
FIG. 2 is a Kyte-Doolittle hydrophobicity plot of rat SVCT1 and SVCT2, generated using a 21-amino-acid window.

Both human and rat SVCT1 and SVCT2 proteins have similar hydropathy profiles, all predicting 12 putative membrane-spanning domains as shown and numbered in FIG. 2. The SVCT1 sequence comprises consensus sites for protein kinases A and C, and N-linked glycosylation. Comparison of the translation products in the presence or absence of microsomes revealed a 15-kilodalton gel shift, suggesting that at least two of the consensus sites in SVCT1 are glycosylated in vivo.

2. Isolation and Analysis of SVCT1 and SVCT2

To clone the genes encoding SVCT1 and SVCT2, an expression cloning strategy using *Xenopus laevis* oocytes as the expression system was employed. It is noted, however, that expression cloning can also be achieved using other mammalian cells, yeast cells, bacterial cells, insect cells, plant cells, or brush border membrane vesicles.

Rat SVCT1 and SVCT2 clones were obtained by isolating SVCT1 cDNA from rat kidney by expression cloning as described in Hediger et al., *Methods Enzymol.* 296:17-52 (1998). The SVCT2 cDNA was subsequently isolated by PCR-based homology screening of a rat brain cDNA library. A 2.5-kb rabbit cDNA with 96% identity to residues 96-505 of the rat SVCT2 was obtained by RT-PCR. Radiotracer and voltage-clamp experiments were performed (at 22° C.) in *Xenopus* oocytes two to seven days after injection with ~25 ng of SVCT1 or SVCT2 cRNA synthesized in vitro. Radiotracer uptake was determined by incubating 6-10 oocytes for 30 or 60 min in standard 100 mM $Na^+$ or $Na^+$-free media with 10-600 μM L-[$^{14}$C]ascorbic acid.

The experimental procedures employed, and the results obtained, were as follows.

2.1 Rat SVCT1 and SVCT2

Cloning of SVCT cDNAs—SVCT1 cDNA was isolated from rat kidney by expression cloning with heterologous expression in *Xenopus* oocytes. Briefly, poly(A)$^+$ RNA was extracted from kidney cortex of normal male Sprague-Dawley rats. This poly(A)$^+$ RNA induced a 30-fold increase in $Na^+$-dependent L-[$^{14}$C]ascorbic acid uptake activity in oocytes compared with control (water-injected) oocytes. Poly(A)$^+$ RNA was size-fractionated using preparative gel electrophoresis, and a positive poly(A)$^+$ RNA fraction inducing maximal L-[$^{14}$C]ascorbic acid uptake activity (1.5-fold enrichment over non-fractionated poly(A)$^+$ RNA) was used to construct a directional cDNA library with the SuperScriptII cDNA synthesis system (supplied by Gibco-BRL). cDNA pools (of ≈2.5×10$^4$ clones each) were screened. A positive pool that increased transport activity to a degree similar to kidney cortex poly(A)$^+$ RNA was sequentially subdivided and analyzed until a single clone (SVCT1) was identified.

SVCT2 cDNA was isolated by PCR-based homology screening of a rat brain cDNA library. First-strand cDNA was prepared by reverse transcription from rat brain poly (A)$^+$ RNA. Sense and antisense degenerate oligonucleotide primers were designed based upon the SVCT1 cDNA sequence (sense, ATH GAR TCN ATH GGN GAY TA (SEQ ID NO: 11), coding for amino acid residues 339-346 of SVCT1, and antisense, CC RAA RAA DAT NGA RAA NCC (SEQ ID NO: 12), residues 468-475) and used for PCR amplification of the brain cDNA. PCR products of the expected size (≈400 bp) were subcloned into the pCRII vector (Invitrogen) and sequenced. A single clone with 80% identity to SVCT1 was labelled using [$^{32}$P]-dCTP and used to screen a rat brain cDNA library constructed in the λgt10 vector. The library (≈4×10$^5$ clones) was screened under high-stringency conditions by washing with 0.1×SSC and 0.1% SDS at 65° C. for 1 h. A positive clone of a 6.5 kb cDNA was isolated and subcloned into pBluescript SK(−). The cDNA sequence was determined on both strands and analyzed using Genetics Computer Group tools. To improve expression in oocytes, an EcoRI site was introduced to the 5'-untranslated region (nucleotide 198) using PCR. Two 6.5-kb SVCT2 cDNA fragments obtained by EcoRI-EcoRI (1.5 kb) and EcoRI-SphI (0.5 kb) digestions, were ligated and subcloned into a blunt-ended dephosphorylated NotI site in the vector pTLN2.

A rabbit cDNA (rbSVCT2) of 1.2-kb in length and with 96% identity to residues 96 to 505 of the rat SVCT2 was obtained by reverse transcription-PCR from rabbit brain mRNA using a set of rat SVCT2 oligonucleotide primers (sense, nucleotides 660-682; antisense, nucleotides 1870-1892). Sequence alignments were performed using the PILEUP program from Genetics Computer Group (Madison, Wis.).

Functional characterization of SVCT1 and SVCT2 in *Xenopus* oocytes—Oocytes were isolated from *Xenopus laevis* (under 2-aminoethylbenzoate anaesthesia), treated with collagenase A and stored at 18° C. in modified Barths' medium. Oocytes were injected with ≈25 ng of SVCT1 or SVCT2 cRNA synthesized in vitro, or water only (control), and incubated 2-7 days before radiotracer or voltage-clamp experiments were performed. Standard $Na^+$ uptake medium comprised 100 mM NaCl, 2 mM KCl, 1 mM $CaCl_2$, 1 mM $MgCl_2$, 10 mM HEPES (pH 7.5 with Tris base). For $Na^+$-free or low-$Na^+$ media, NaCl was replaced by equimolar choline chloride; likewise, $Cl^-$ was replaced by gluconate for Cl⁻-free medium. For pH-sensitivity experiments, Na⁺ media were buffered at pH 5.5-8.0 using 0-5 mM MES, 0-5 mM HEPES and 0-5 mM Tris base. L-Ascorbic acid-containing solutions were freshly-prepared (without dithiothreitol) and used immediately.

Radiotracer uptake was determined by incubating 6-10 oocytes for 30 or 60 min in standard Na⁺ or Na⁺-free media (at 22° C.) with 10-600 µM L-[1-$^{14}$C]ascorbic acid (final specific activity 0.3 GBq/mmol). Oocytes were solubilized with 10% SDS and [$^{14}$C]-content was measured by liquid scintillation counting. A two-microelectrode voltage-clamp was used to measure currents in control oocytes and oocytes injected with rat SVCT1 or rat SVCT2 cRNA. Microelectrodes (resistance 0.5-5 MΩ) were filled with 3 M KCl. Oocytes were superfused at 22° C. in standard Na⁺ medium and clamped at a holding potential ($V_h$) of −50 mV. For continuous current monitoring at $V_h$=−50 mV, the current was low-pass filtered at 20 Hz (sampling at 1 Hz). Additionally, step-changes in membrane potential ($V_m$) were applied (from +50 mV to −150 mV in 20-mV increments), each for a duration of 100 ms, before and after the addition of substrate; current was low-pass filtered at 500 Hz and digitized at 5 kHz. Test solutions were always washed out with substrate-free medium (100 mM choline chloride) at pH 7.5 for several minutes. Steady-state data (obtained by averaging the points over the final 16.7 ms at each $V_m$ step when step-changes were applied) were fitted to equation (1) below, for which I is the evoked current (i.e., the difference in steady-state current measured in the presence and absence of substrate), $I_{max}$ the derived current maximum, S the concentration of substrate S (Na⁺ or L-ascorbic acid), $$K_{0.5}^S$$

the substrate concentration at which current was half-maximal, and $n_H$ the Hill coefficient for S. (For radiotracer experiments, I was replaced with velocity V and $I_{max}$ replaced with the derived maximal velocity, $V_{max}$.)

$$I = \frac{I_{max} \cdot S^{n_H}}{(K_{0.5}^S)^{n_H} + S^{n_H}} \quad (1)$$

Observed data indicate that SVCT1 and SVCT2 each mediate saturable, Na⁺-dependent L-ascorbic acid transport in an electrogenic manner. L-[$^{14}$C]Ascorbic acid uptake (in 100 mM NaCl) followed Michaelis-Menten-type saturation kinetics with high apparent affinity for L-ascorbic acid. Uptakes were not affected by replacement of chloride with gluconate, indicating that neither isoform was Cl⁻-dependent.

Figure 4A:
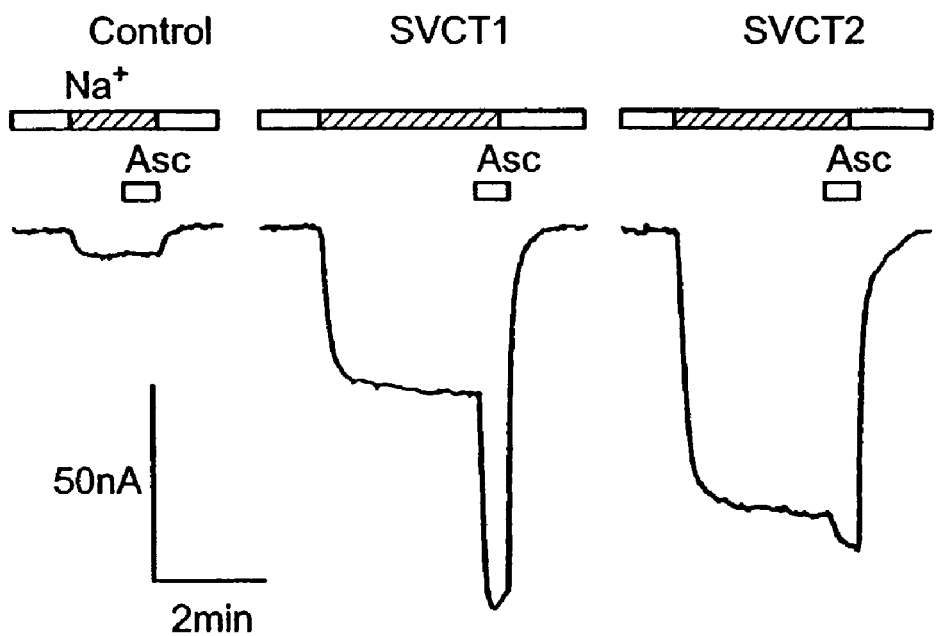
FIG. 4A depicts typical current recordings from a voltage-clamped (1-50 mV) control oocyte or oocytes expressing rat SVCT1 and SVCT2, all from a single batch of oocytes (the approximate baseline current in standard $Na^+$ medium at pH 7.5 is indicated by dashed lines)
Figure 4B:
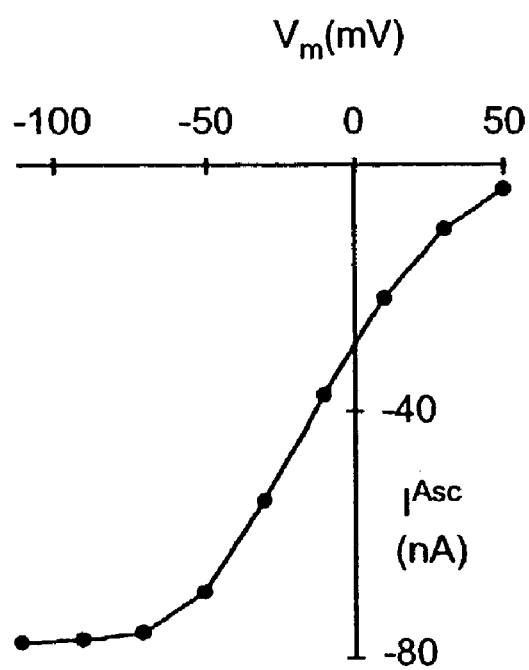
FIG. 4B depicts the current/voltage (I/V) relationship for rat SVCT1 at 500 μM (saturating) L-ascorbic acid (at 100 mM $Na^+$)

In the presence of Na⁺, L-ascorbic acid evoked reversible inward currents of up to −100 nA in oocytes expressing SVCT1 and up to −10 nA in oocytes expressing SVCT2 (FIG. 4A). Evoked currents in control oocytes were −1 nA±0.5 nA (s.d.) at 500 µM L-ascorbic acid. Transporter-associated currents were investigated in detail for SVCT1 and, where possible, our findings were supported by data from radiotracer experiments for SVCT1 and SVCT2. In oocytes expressing SVCT1, the L-ascorbic acid-evoked currents (at saturating L-ascorbic acid) showed a curvilinear dependence on membrane potential ($V_m$) (FIG. 4B), saturating with hyperpolarization (−70 mV). The current/voltage relationship was roughly linear between −50 mV and +30 mV (tending toward a zero current asymptote at positive $V_m$) with no reversal of the currents observed up to +50 mV. At −50 mV, $$K_{0.5}^{Asc}$$

Figure 4C:
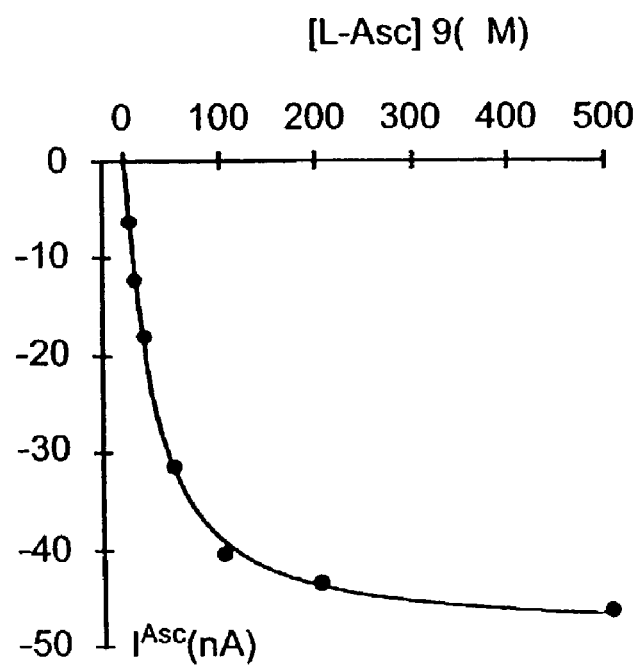
FIG. 4C illustrates L-ascorbic acid saturation kinetics for rat SVCT1 at 100 mM $Na^+$ and at −50 mV.
Figure 4D:
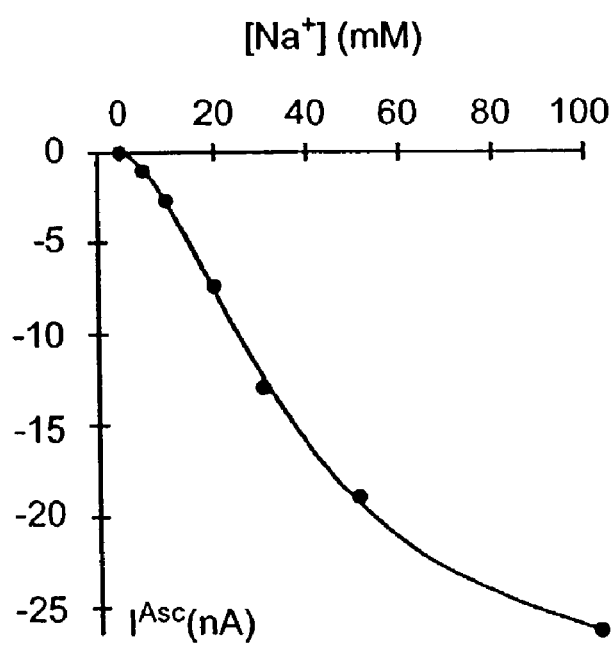
FIG. 4D illustrates $Na^+$ saturation kinetics of the currents evoked by 200 μM L-ascorbic acid for rat SVCT1 at −50 mV.

(L-ascorbic acid concentration at which currents were half-maximal) was 30 µM (FIG. 4C) with $n_H$≈1. The Hill coefficient ($n_H$) for Na⁺ was ≈2 (FIG. 4D).

$$K_{0.5}^{Na}$$

Figure 4E:
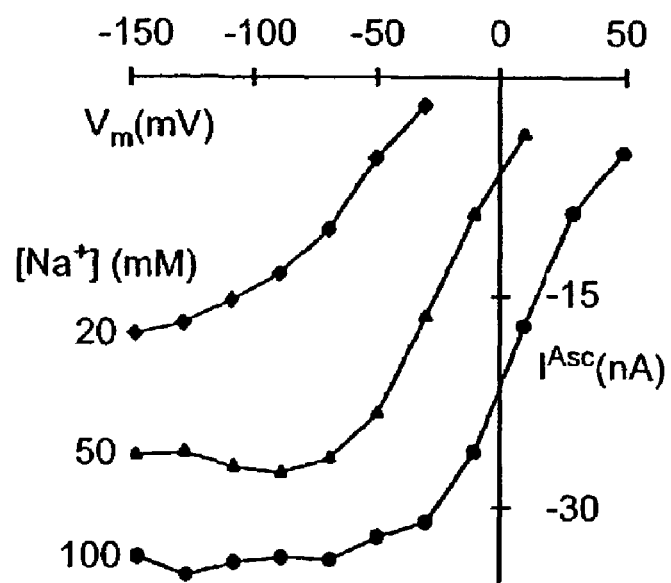
FIG. 4E depicts the effect of $Na^+$ on the I/V relationship for rat SVCT1 (at 200 μM L-ascorbic acid)

(at 200 µM L-ascorbic acid) was 40 mM at −50 mV;

$$K_{0.5}^{Na}$$

was not significantly different at hyperpolarized $V_m$, but rose at depolarized $V_m$. These data suggested that two Na⁺ bind to SVCT1 and that binding is voltage-sensitive. SVCT1-mediated L-ascorbic acid transport is driven by the electrochemical gradient for Na⁺ since, at any given $V_m$, the current evoked by 200 µM L-ascorbic acid was greatest at higher Na⁺ concentrations (FIG. 4E). The evoked currents obtained at 100 mM Na⁺ saturated at less negative $V_m$, and with a larger maximal current than those obtained at 50 and 20 mM Na⁺. Following step-changes in voltage, SVCT1 exhibited presteady-state currents (decaying with time constants 10-40 ms). These presteady-state currents were sensitive to changes in extracellular Na⁺ concentration and (in analogy to other ion-coupled transporters) are due in part to binding/dissociation of the driving ion (in this case Na⁺) to the transporter. Switching from 0 to 100 mM Na⁺ in the absence of L-ascorbic acid resulted in a small inward current in control oocytes (FIGS. 4A, 4G) but a much larger current in oocytes expressing either SVCT1 or SVCT2. Addition of L-ascorbic acid in the presence of Na⁺ evoked still larger inward currents. These observations suggested that SVCT1 and SVCT2 can additionally exhibit a Na⁺ leak (uniport) current (similar to the leak pathways in other ion-coupled transporters) that is as much as half the magnitude of the current associated with Na⁺/L-ascorbic acid cotransport (FIG. 4G).

Figure 3:
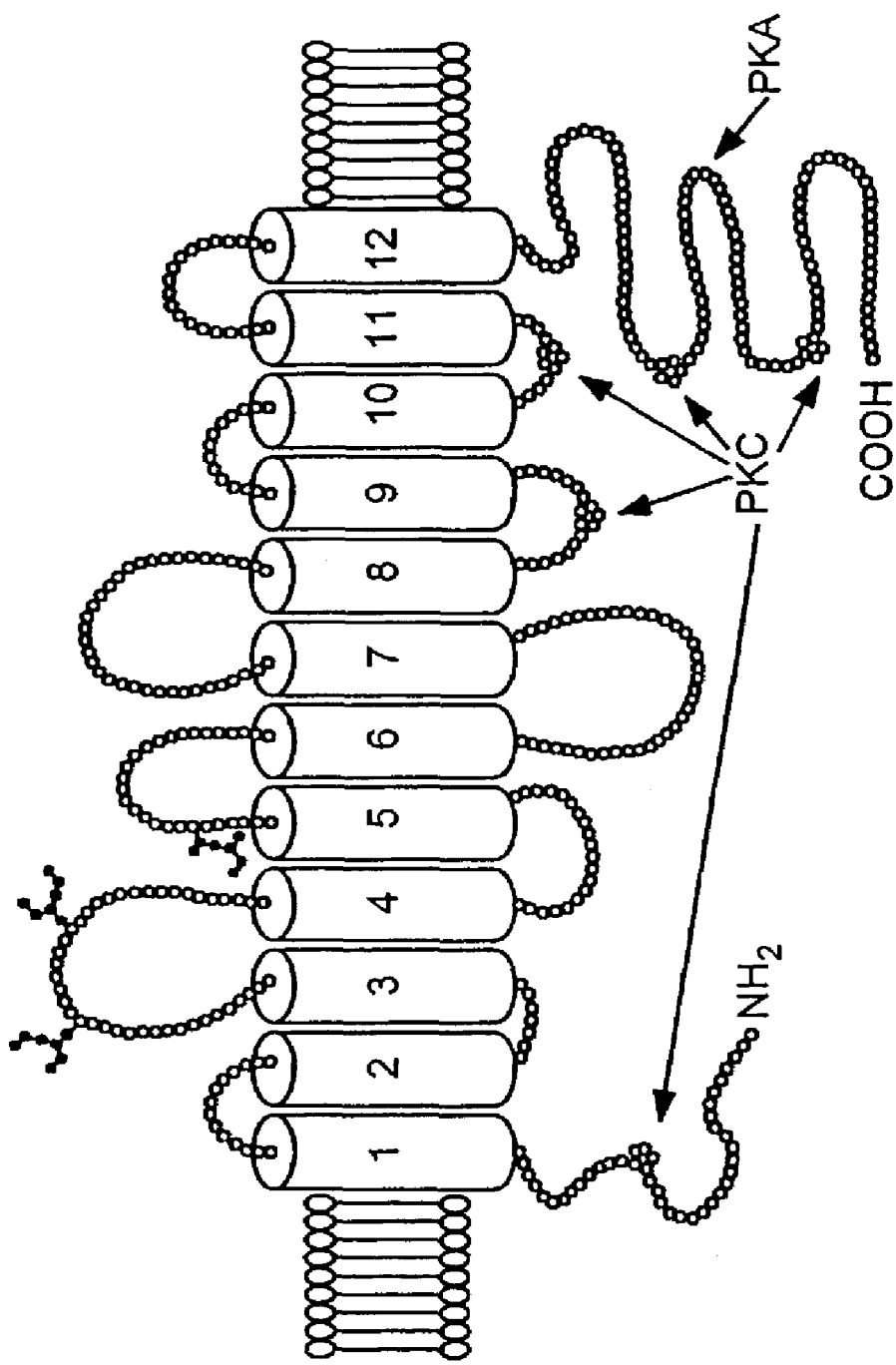
FIG. 3 is a membrane-topology model of rat and human SVCT1 based on hydropathy profiles.
Figure 4F:
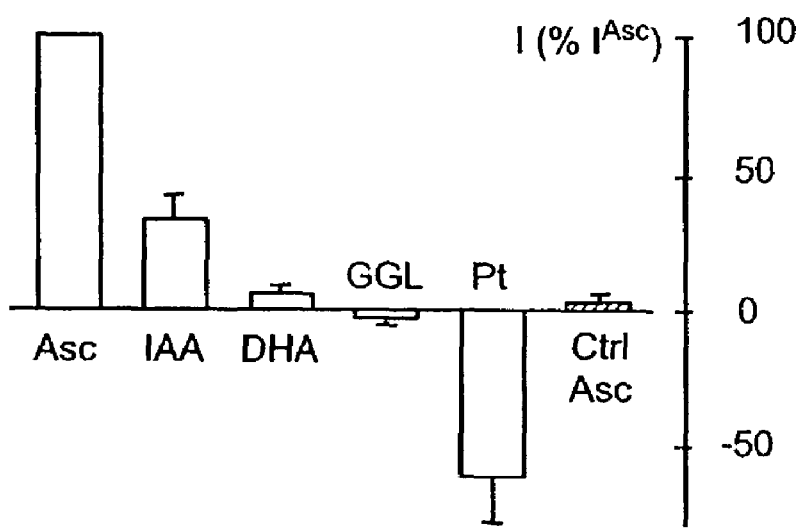
FIG. 4F demonstrates the substrate selectivity of rat SVCT1.
Figure 4G:
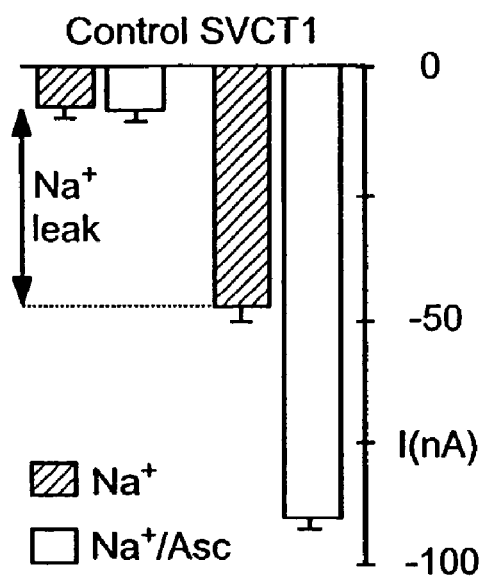
FIG. 4G shows a comparison of currents due to $Na^+$ leak (uniport) and $Na^+$/L-ascorbic acid co-transport.
Figure 4H:
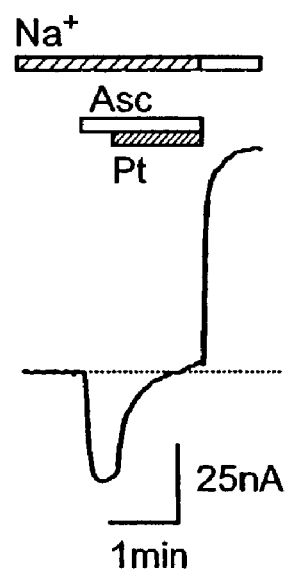
FIG. 4H illustrates phloretin (Pt) inhibition of the L-ascorbic acid-evoked current in rat SVCT1.
Figure 4I:
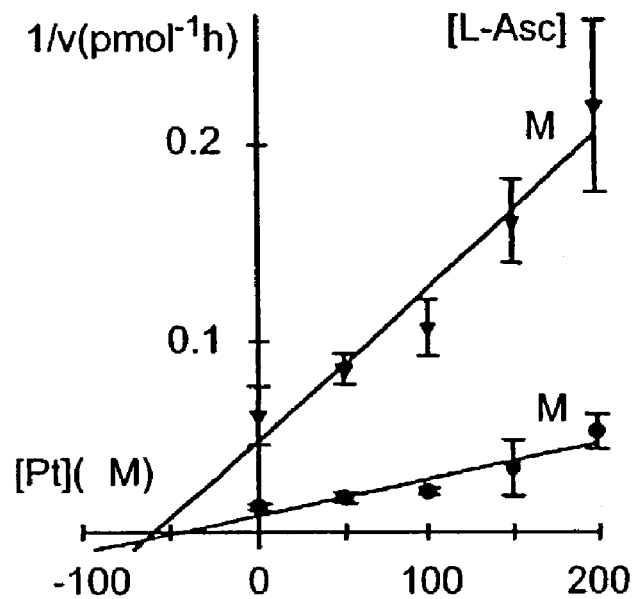
FIG. 4I illustrates a Dixon analysis of phloretin inhibition.
Figure 4J:
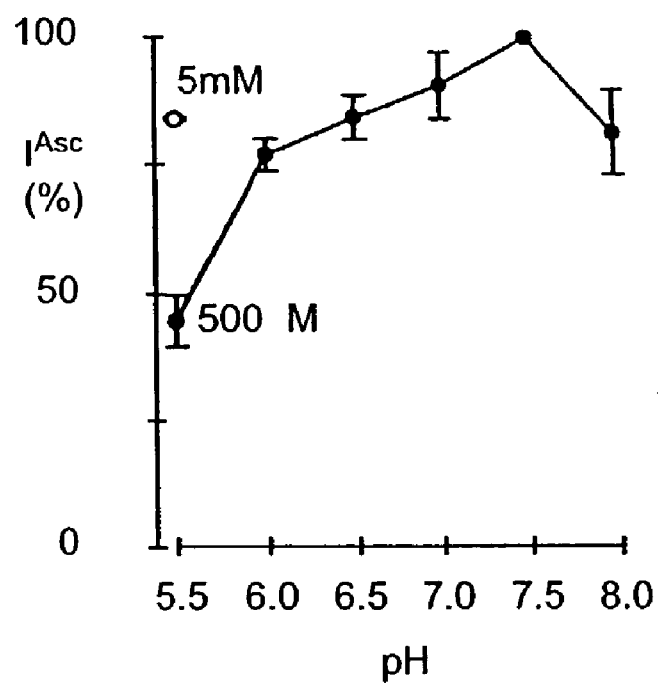
FIG. 4J shows the pH dependence of L-ascorbic acid-evoked currents in rat SVCT1.

As shown in FIG. 4F, SVCT1 was highly selective for L-ascorbic acid, which evoked much larger currents than did D-isoascorbic acid (≈30% that for L-ascorbic acid) or dehydroascorbic acid (≈5%). (Dehydroascorbic acid failed to evoke a current in control oocytes.) D-Glucose, uracil, and intermediates of vitamin C metabolism (such as L-gulono-γ-lactone) were excluded. Several test compounds, including aspirin (acetyl-salicylic acid), xanthine, sulfinpyrazone and phlorizin, each evoked tiny outward currents in oocytes expressing SVCT1 and resulted in modest inhibition of the SVCT1- or SVCT2-mediated L-[$^{14}$C]ascorbic acid uptake—i.e., they exhibited characteristics of weak blockers. Phloretin evoked a sizable outward current in oocytes expressing SVCT1 (FIG. 3F). This effect is probably attributable to phloretin blocking the Na⁺ leak current. In addition, phloretin blocked the inward current evoked by L-ascorbic acid (FIG. 4H) and inhibited L-[$^{14}$C]ascorbic acid uptake by SVCT1 or SVCT2. Dixon analysis of L-[$^{14}$C]ascorbic acid uptake for SVCT1 (FIG. 4I) revealed that phloretin was a non-competitive inhibitor with $K_i \approx 65$ µM. Meanwhile, phloretin inhibited the Na$^+$ leak current with apparent $K_i \approx 100$ µM. The similarity of these values for the effects of phloretin on both the cotransport and uniport modes of the transport cycle suggests that phloretin interacts with SVCT1 at a single locus on the protein. The evoked currents in SVCT1 were sensitive to changes in extracellular pH (FIG. 4J). Those at pH 5.5 were 50% smaller than those at pH 7.5 but were partially restored by the addition of excess L-ascorbic acid (5 mM). A similar pattern of pH-sensitivity was observed for SVCT2 in radiotracer experiments. This pH-sensitivity is probably a result of reduced binding affinities for L-ascorbic acid rather than less available L-ascorbic acid in the deprotonated (1−) form, since >95% is in the deprotonated form at pH 5.5 ($pK_{a1}$=4.2). Although the small currents obtained for SVCT2 hampered its characterization, radiotracer experiments did not reveal any functional differences between the SVCT isoforms. The activities described for SVCT1 and SVCT2 expressed in oocytes were consistent with those described for several mammalian tissues (in vesicles, isolated tissues or cultured cell lines) with regard to the following characteristics: (i) high apparent affinity for L-ascorbic acid ($K_{0.5}^{Asc}$ of 10-100 µM); (ii) a preference for L-ascorbic acid>D-isoascorbic acid>dehydroascorbic acid; and (iii) Na$^+$ dependence.

Northern-blot analysis—Total RNA was isolated from rat tissues and cell culture of murine MC3T3-E1 osteoblasts followed by oligo(dT) selection. Poly(A)$^+$ RNA (3 µg/well) was separated on a formaldehyde-agarose (7%/1%) gel and blotted onto a nitrocellulose filter. A 0.35-kb Bg/II digestion product from SVCT1 cDNA (nucleotides 425-773) and a 3.1-kb HindIII digestion product of SVCT2 cDNA (nucleotides 1-3101) were labelled with [$^{32}$P]-dCTP. The filters were hybridized at 42° C. in 50% formamide, and washed in 5×SSC/0.1% SDS at 50° C. for 2×30 min, then in 0.1×SSC/0.1% SDS at 65° C. for 3×20 min.

Striking differences between SVCT1 and SVCT2 in terms of tissue distribution in rat were found. Northern-blot analysis using a probe for SVCT1 revealed intense bands at ≈2.5 kb and ≈4.0 kb in rat kidney, intestine, and liver, whereas probing for SVCT2 RNA resulted in a weaker signal at ≈6.5 kb for those tissues. Using in situ hybridization of rat tissues, SVCT1 was localized to the straight segment (S3) of the proximal tubule in the kidney, consistent with studies of rat kidney L-ascorbic acid transport in vitro. In the small intestine, SVCT1 and SVCT2 mRNAs were present in enterocytes. In liver, SVCT1 but not SVCT2 was detected in hepatocytes. Both isoforms were detected in epithelial cells of the bronchiole and epididymis.

SVCT2 was abundantly expressed in an array of neural, neuroendocrine, exocrine and endothelial tissues as well as in osteoblasts. In Northern-blot analysis of rat tissue, a strong SVCT2 signal was obtained for brain at ≈6.5 kb. The mRNA was localized to neurons throughout the CNS. The distribution closely matched the sites of rapid neuronal accumulation observed in mouse brain following intravenous L-[$^{14}$C]ascorbic acid injection and is consistent with the view that neurons take up L-ascorbic acid (released by astroglia). SVCT2 was also detected in the meninges and choroid plexus, suggesting that SVCT2 may facilitate entry of L-ascorbic acid into the cerebrospinal fluid compartments. In the retina, SVCT2 labelling was observed exclusively in the inner nuclear layer (the site of bipolar, amacrine, and horizontal cell bodies).

L-Ascorbic acid is believed to be crucial in protecting components of the eye (e.g., the lens and cornea) from radiation-induced damage. Since the levels of L-ascorbic acid in the aqueous humor (anterior chamber) in diurnal mammals can be around 20-fold greater than in nocturnal mammals, investigations were undertaken to determine whether the distribution of SVCT isoforms in the eye differed between the rat (nocturnal) and the rabbit (diurnal-nocturnal). In the rat, neither SVCT1 nor SVCT2 was detected in the ciliary body (which secretes aqueous humor) or iris. However, in the albino rabbit, SVCT2 was abundantly expressed in the pigmented epithelium of the ciliary body, and moderately expressed in the deeper layers of the corneal epithelium. This SVCT2 distribution was consistent with the known sites of L-ascorbic acid concentration in the rabbit eye, and the characteristics of SVCT2 reflected those of a Na$^+$-dependent, L-ascorbic acid transport activity expressed in bovine pigmented ciliary epithelial cells. In the rat, SVCT1 and SVCT2 were each detected in exocrine cells of the lacrimal gland; there, the supply of L-ascorbic acid to the tear fluid may provide sufficient anti-oxidant protection in nocturnal species.

SVCT2 was expressed in several components of the endocrine system, including the anterior pituitary, in which L-ascorbic acid is important in α-amidation of peptide hormones. Labelling was also observed in the intermediate lobe but not in the posterior lobe. SVCT2 was abundantly expressed throughout the pancreas and in adrenal cortex. In the adrenal gland, L-ascorbic acid is critical for the copper-associated dopamine-β-hydroxylase involved in noradrenalin synthesis. SVCT2 was detected in gastric glands, extending from the base to the isthmus. Autoradiographic studies in mouse demonstrated rapid accumulation of L-ascorbic acid into the gastric mucosa following intravenous injection. Taken together these observations implicate SVCT2 in the basolateral uptake of L-ascorbic acid, for secretion by the gastric gland, aiding dietary iron absorption. An intense SVCT2-related signal was obtained in Northern-blot analysis of poly(A)$^+$ RNA from the murine osteoblast MC3T3-E1 cell line. SVCT2-mediated L-ascorbic acid transport into osteoblasts may account for the adequate supply of the vitamin to maintain Fe$^{2+}$ required by hydroxylases involved in collagen synthesis. Among immune system organs, SVCT2 was detected by Northern-blot in the spleen and thymus. In testis, SVCT2 was expressed in interstitial cells and spermatocytes.

In situ hybridization Digoxigenin-labelled antisense and sense run-off transcripts were synthesized using the Genius Kit (supplied by Boehringer-Mannheim). Rat SVCT1 cRNA probes were transcribed from a PCR fragment that contained about 1.2 kb of SCVT1 cDNA (nucleotides 161-1411) flanked by promoter sites for SP6 and T7 polymerase. Rat SVCT2 cRNA probes were transcribed from a plasmid vector pBluescript SK(B) which contained 3.1 kb of the SVCT2 sequence (nucleotide 1 to 3101). Transcripts were alkali-hydrolyzed to an average length of 200-400 nucleotides. In situ hybridization was performed on 10-µm cryosections of fresh-frozen tissue. Sections were immersed in slide mailers in hybridization solution of composition 50% formamide, 5×SSC, 2% blocking reagent, 0.02% SDS and 0.1% N-laurylsarcosine, and hybridized at 70° C. for 16 h with probe concentrations of ≈200 ng/ml. Sections were then washed 3 times in 2×SSC and for 2×30 min in 0.2×SSC at 70° C. The hybridized labelled probes were visualized using anti-digoxigenin Fab fragments and BCIP/NBT substrate. Sections were developed in substrate solution for 16 h, rinsed in 100 mM Tris, 100 mM NaCl, 1 mM EDTA (pH 9.5), and coverslipped. For in situ hybridization of rbSVCT2 in rabbit, sense and antisense rbSVCT2 cRNA probes were prepared by RT-PCR based on the same oligonucleotide sequence from rat SVCT2 additionally flanked by the SP6 and T7 RNA polymerase promoter sequences. In situ hybridization was performed on 10-μm cryosections from the eye of a New Zealand albino rabbit (as described above for rat).

Hybrid depletion—Antisense oligonucleotides were generated against nucleotides 18-42 of rat SVCT1, and nucleotides 383-405 of rat SVCT2. These were annealed (at 0.25 μg/μl, in 50 mM NaCl at 42° C.) for 15 min with 0.5 μg/μl poly(A)$^+$ isolated from rat kidney cortex, small intestine or adrenal glands. Samples were then cooled on ice and injected into oocytes (≈25 ng/oocyte), before performing radiotracer assays as described above. The efficacy of the annealing process, and the suitability of the antisense oligonucleotides, was established using SVCT1 or SVCT2 cRNA. It was found that annealing with the appropriate antisense oligonucleotide abolished L-ascorbic acid transport activity, with no appreciable cross-inhibition between SVCT isoforms.

L-[$^{14}$C]Ascorbic acid uptake was 3-fold higher in oocytes injected with intestinal RNA than in control oocytes. The induced activity was Na$^+$-dependent (not shown) and abolished by hybridization with antisense oligonucleotide against SVCT1, suggesting that SVCT1 is the predominant L-ascorbic acid transport system in the small intestine. Similar results were obtained for kidney, and data for adrenal gland suggested that expression of SVCT2 and SVCT1 can together account for the increased uptake in RNA-injected oocytes. Therefore SVCT1 and SVCT2 appear to be the predominant L-ascorbic acid transport systems (at least for $$K_{0.5}^{Asc}$$

of similar order) in the tissues tested.

2.2. Human SVCT1 and SVCT2

Molecular cloning of human SVCT1 cDNA—RNA was isolated from human kidney by guanidinium isothiocyanate/CsCl centrifugation followed by poly(A)$^+$ selection using oligo(dT)-cellulose columns. A λgt10 cDNA library was constructed from the human kidney poly(A)$^+$ RNA using the SuperScript II cDNA synthesis kit (from Life Technologies). cDNA was synthesized using an oligo(dT) primer and ligated to EcoRI-NotI adaptors. cDNA fragments of 2-4 kilobases (kb) in length were isolated and ligated to EcoRI-cleaved λgt10 DNA. After packaging using the Gigapack II Gold cloning kit (from Stratagene), phage (4 H 10$^5$ pfu) was plated and transferred to replicate filters. A human EST clone (accession number AA811090) homologous with rat SVCT1 (AF080452) was labeled with [$^{32}$P]-dCTP. The filters were then hybridized with the EST probe overnight at 42° C. in buffer containing 50% formamide, 5×SSC, 50 mM sodium phosphate (buffered to pH 6.8), 2× Denhardt's solution, and 100 mg/ml denatured salmon sperm DNA. The filters were washed under high stringency conditions (0.1× SSC and 0.1% SDS at 65° C. for 1 h). Positive clones were isolated and subcloned into pBluescript SK(−) vector. cDNA fragments were sequenced and analyzed using GCG tools (from Genetics Computer Group) to identify human clones related to SVCT1 previously cloned from rat and rabbit as described above.

Construction of the human SVCT2 cDNA—Oligonucleotide primers (5' ATG ATG GGT ATT GGT AAG AAT ACC 3' (SEQ ID NO: 13) and 5' AGC AAG GAA CTA CAG ATA CAT GCC 3' (SEQ ID NO: 14)) based on the YSPL2 sequence (listed in GenBank as human SVCT2, and with accession number AF058319) and a similar sequence (D87075) were used for RT-PCR amplification, using the Advantage cDNA PCR kit (from Clontech) and human kidney total RNA, to generate the human SVCT2 cDNA (2010 bp), the identity of which was confirmed by partial sequencing (≈500 bp) from the 5' end.

Functional characterization in Xenopus oocytes—SVCT1 and SVCT2 cDNAs were subcloned into the pTLN2 vector (to improve functional expression in oocytes) and used for cRNA synthesis in vitro using the MEGAscript kit and T7 RNA polymerase (from Ambion). Oocytes were isolated from Xenopus laevis, treated with collagenase A and maintained at 18° C. in modified Barths' medium. Oocytes were injected with 15 ng SVCT1 or SVCT2 cRNA or water only. The radiotracer uptake and voltage-clamp experiments described below were conducted 2-5 days post-injection in standard medium of composition 100 mM NaCl, 2 mM KCl, 1 mM CaCl$_2$, 1 mM MgCl$_2$, and 10 mM HEPES (buffered to pH 7.5 with Tris base). For low-Na$^+$ or Na$^+$-free media, NaCl was replaced with choline chloride. For pH-dependence experiments, Na$^+$ media were buffered to between pH 5.5 and pH 8.0 using 0-5 mM MES, 0-5 mM HEPES and 0-5 mM Tris base. L-Ascorbic acid-containing solutions were always freshly prepared and used immediately. Radiotracer uptake was determined by incubating 8-12 oocytes for 30 min (within the time-course of linear uptake) in standard Na$^+$, low-Na$^+$ or Na$^+$-free media with 10-500 μM L-[1-$^{14}$C] ascorbic acid (final specific activity ≈0.3 GBq/mmol). Oocytes were solubilized with 10% SDS and carbon-14 content measured by liquid scintillation counting. A two-microelectrode voltage-clamp was used to measure currents associated with SVCT1 expressed in oocytes. Oocytes were superfused at 22° C. in standard Na$^+$ medium and clamped at −50 mV. Current was continuously monitored by sampling at 1 Hz. Test solutions were always washed out with substrate-free, Na$^+$-free medium at pH 7.5 for several minutes. Once again, saturation kinetics data were fit to a modified Hill equation in which I and I$_{max}$ were replaced by uptake V and maximal velocity V$_{max}$ for analysis of radiotracer uptake data.

Chromosome mapping of the SLC23A2 gene encoding human SVCT1—The SLC23A2 gene, which encodes human SVCT1, was mapped using fluorescence in situ hybridization. 1.0 μg of SVCT1 cDNA clone was labeled with digoxigenin-11-dUTP, co-precipitated with 50 μg of tRNA and resuspended in 1× TE at 100 μg/ml. Hybridization of metaphase chromosome preparations from peripheral blood lymphocytes (obtained from a healthy male volunteer) was performed with labeled SVCT1 probe (20 μg/ml) in Hybrisol VI. Digoxigenin-labeling was detected using the Oncor kit, and metaphase chromosomes were counterstained with 4,6-diamidino-2-phenylinode-dihydrochloride (DAPI). The map position of the SLC23A2 gene was determined by visual inspection of the fluorescent signal on the DAPI-stained metaphase chromosomes.

Figure 5:
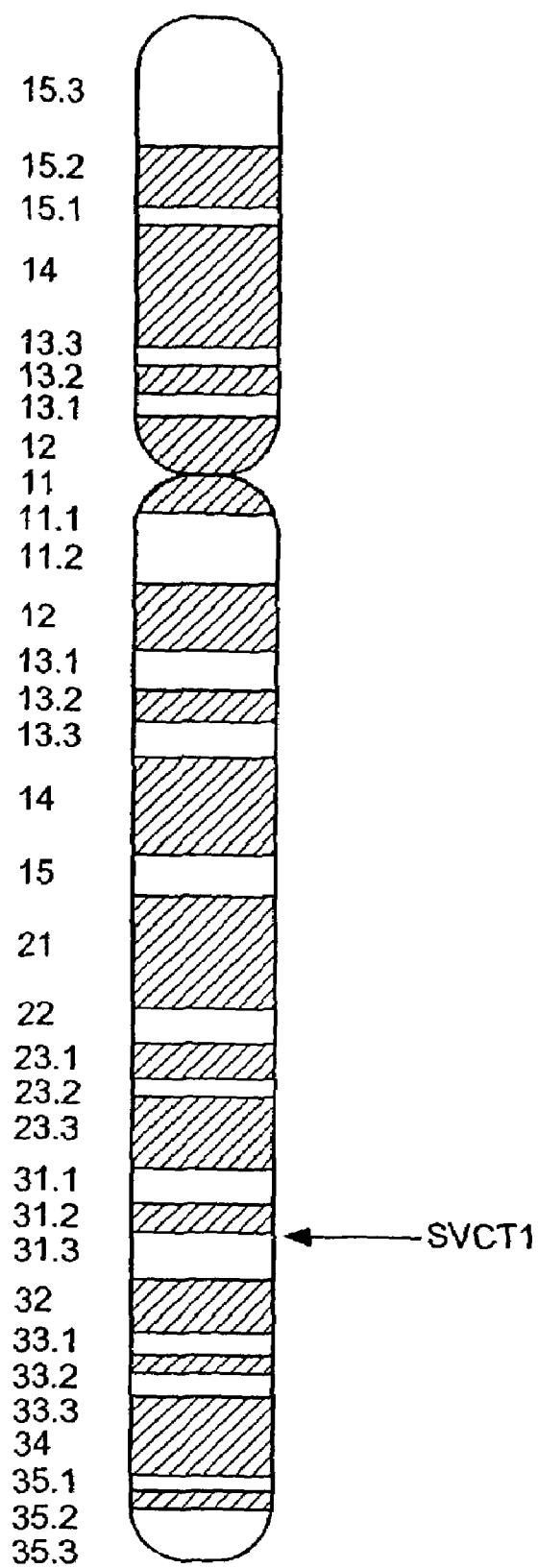
FIG. 5 is an ideogram of human chromosome 5 showing the location of the gene encoding SVCT1.
Figure 6:
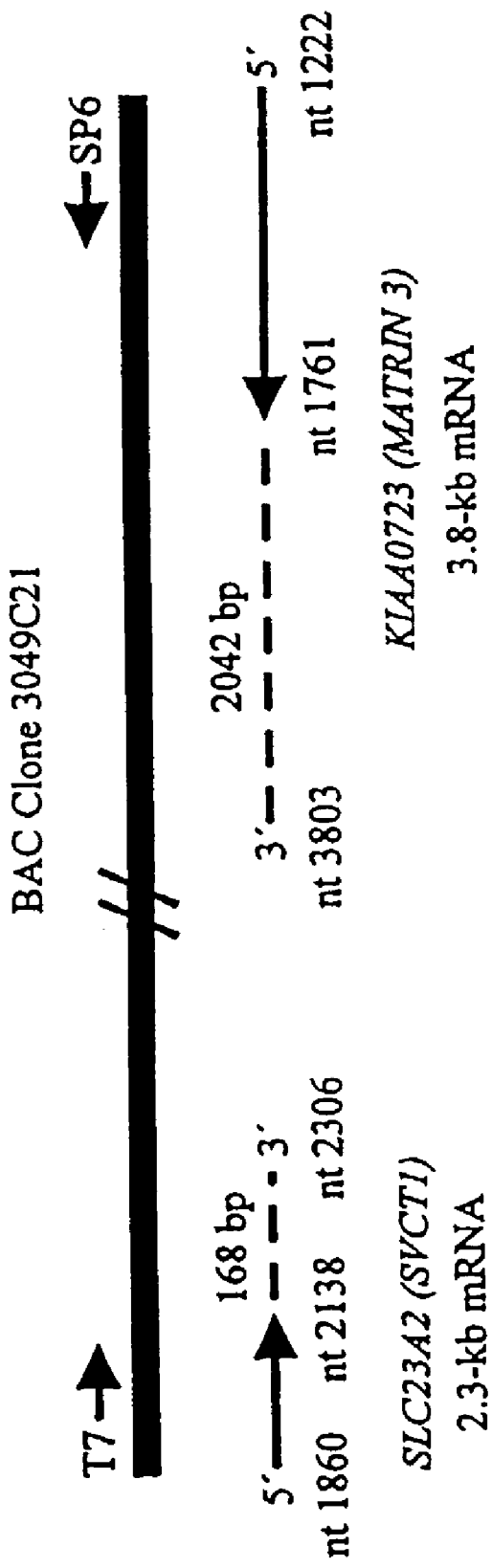
FIG. 6 illustrates the genomic localization of the SLC23A2 and MATRIN3 genes.
Figure 7:
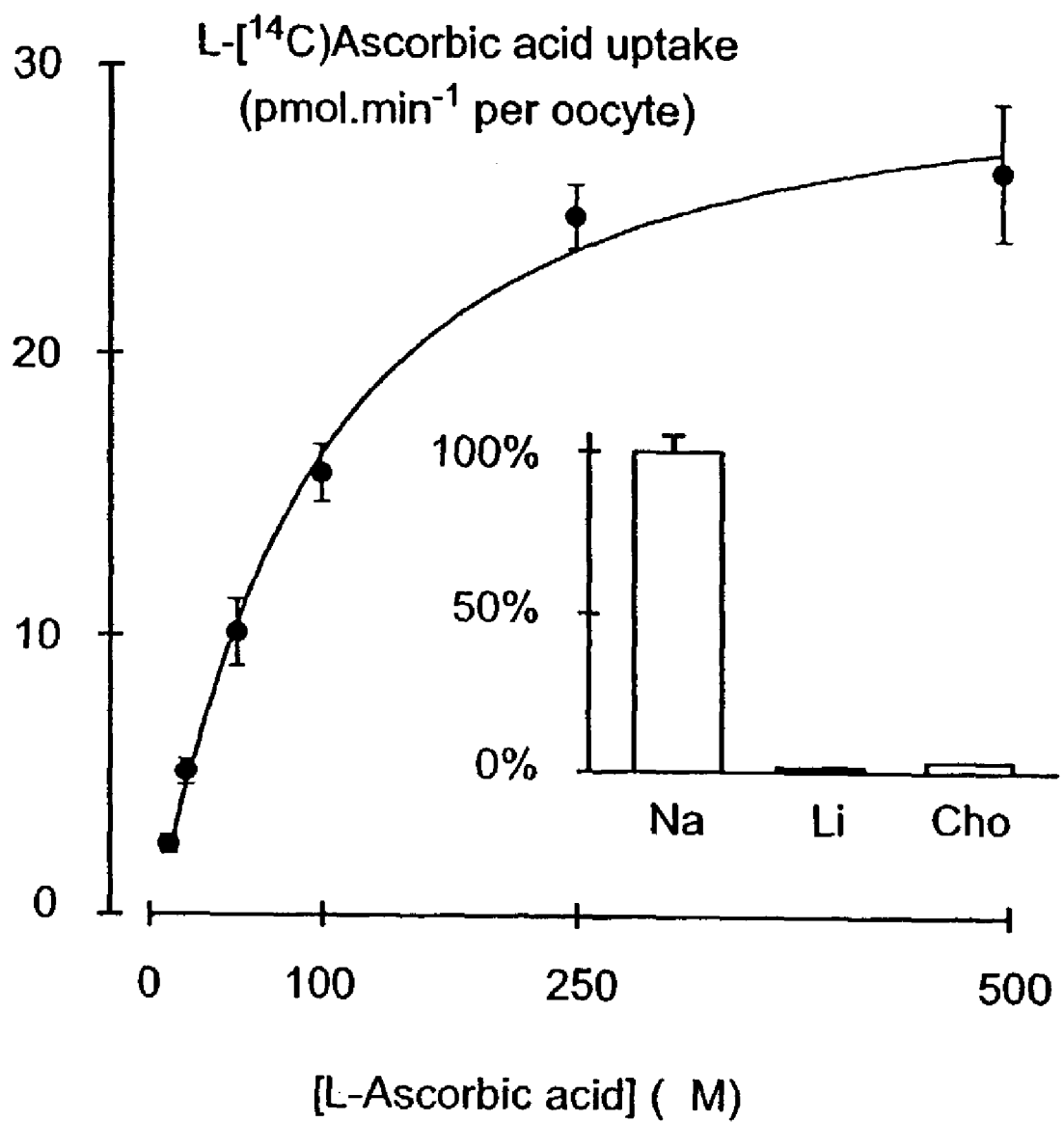
FIG. 7 graphically illustrates the transport characteristics of SVCT1 expressed in oocytes based on [$^{14}$C]ascorbate isotope flux studies.

Fluorescence in situ hybridization with the 2306-bp cDNA probe permitted assignment of the SLC23A2 gene to chromosome 5 in band q31.2-31.3 (FIG. 5). Of 23 metaphases, labeling was detected on the long arm of chromosome 5 in 21 cells, of which 10 displayed labeling on both chromosomes 5. Analysis using the Stanford G3 Radiation Hybrid Panel revealed that SLC23A2 is closely linked to marker D5S500 (LOD score 10.82). A BLAST search based on the full-length SVCT1 sequence identified BAC clone 3049C21, and sequence analysis revealed that BAC3049C21 contains both the 3' end of SLC23A2 and the 3' end of MATRIN 3 (a gene encoding a cell matrix protein) in opposing orientation (FIG. 6).

Northern analysis—Human multiple-tissue Northern blots were probed with the $^{32}$P-labeled human EST (SVCT1) probe or with SVCT2 probe (a PCR product corresponding to the first 1 kbp of D87075). The filters were hybridized at 42° C. in 50% formamide, then twice-washed in 5×SSC/0.1% SDS at 50° C. for 30 min and three times in 0.1×SSC/0.1% SDS at 65° C. for 20 min.

Transport activity associated with SVCT1 expressed in oocytes—Uptake of 500 µM L-[$^{14}$C]ascorbic acid was stimulated 200-fold and in oocytes expressing SVCT1 (15.5±1.2 pmol/min per oocyte) compared with water-injected control oocytes. With reference to FIG. 6, L-Ascorbic acid uptake followed Michaelis-Menten-type saturation kinetics, with half-maximal concentration ($K_{0.5}$) of ≈90 µM and Hill coefficient ($n_H$) for L-ascorbic acid close to 1. Uptake was effectively abolished when extracellular Na$^+$ was replaced by choline, indicating that L-ascorbic acid uptake is Na$^+$-dependent (FIG. 6, inset graph), with $K_{0.5}$ for Na$^+$ of 15-25 mM. It was found that Li$^+$ was unable to substitute for Na$^+$ in driving SVCT1-mediated transport.

In voltage-clamped oocytes expressing SVCT1, L-ascorbic acid evoked reversible inward currents of up to −150 nA in the presence of extracellular Na$^+$ (FIG. 8A), whereas 500 µM L-ascorbic acid evoked currents of only −1±0.5 nA (mean ±s.d.) in control oocytes. Oocytes were voltage-clamped at −50 mV in the absence (blank boxes) or presence (hatched boxes) of Na$^+$ at pH 7.5. The oocytes were superfused with 500 µL-ascorbic acid for the periods shown by the solid bar (or additionally 100 µM phloretin, gray box), before washing out with Na$^+$-free, substrate-free medium.

Figure 8A:
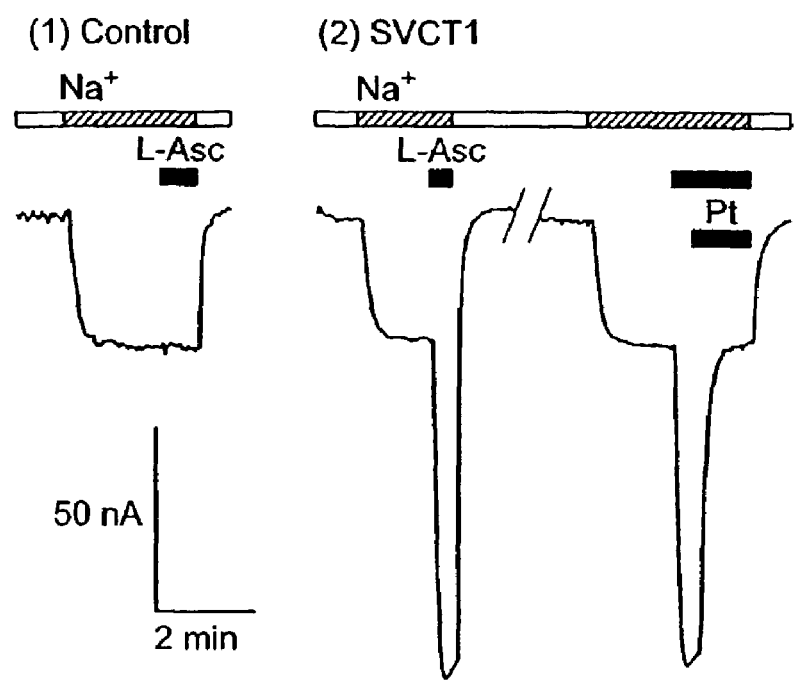
FIG. 8A graphically illustrates the results of voltage-clamp experiments to determine transport properties, and shows typical current recordings from (1) a control oocyte and (2) an oocyte expressing human SVCT1 from the same batch.
Figure 8B:
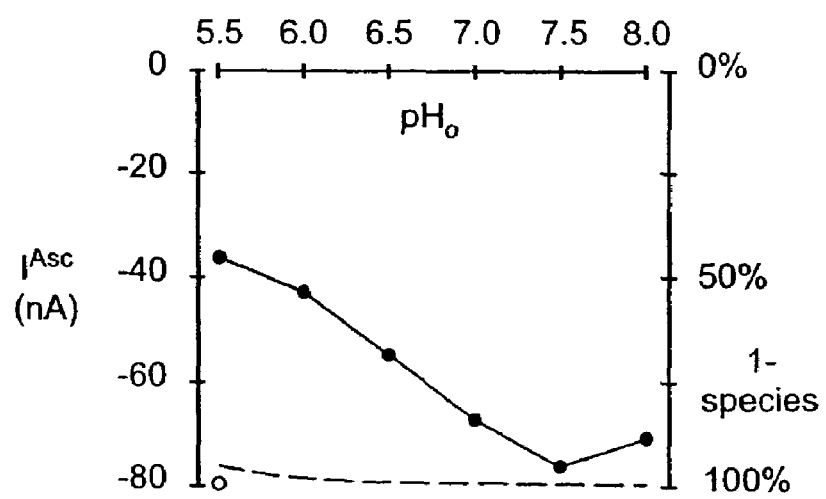
FIG. 8B shows the pH dependence of L-ascorbic acid-evoked currents in human SVCT1.

The currents evoked by 500 µM L-ascorbic acid were pH-sensitive at −50 mV (FIG. 8B). The figure illustrates the pH dependence of the SVCT1-mediated currents (left axis) evoked by 500 µM (filled circle) or 5 mM (open circle) L-ascorbic acid at −50 mV in Na$^+$ medium. The dashed line represents the approximate proportion of L-ascorbic acid present in its deprotonated form (right axis) in the medium, calculated from the Henderson-Hasselbalch equation using $pK_{a1}$ for L-ascorbic acid of 4.17. Maximum current was obtained at pH 7.5, with a small reduction in current at pH 8.0, but a larger reduction in the current at lower pH. The >60% reduction in current observed at pH 5.5 (compared with pH 7.5) was entirely restored by increasing the L-ascorbic acid concentration to 5 mM. Since over 95% of the L-ascorbic acid ($pK_{a1}$≈4.2) is present in the deprotonated form at pH 5.5, the significant reduction in transport activity at low pH is not due to the reduction of the effective L-ascorbic acid (1−) species, but rather it is attributable to a reduction in the binding affinity of the transporter for L-ascorbic acid at low pH.

Figure 9:
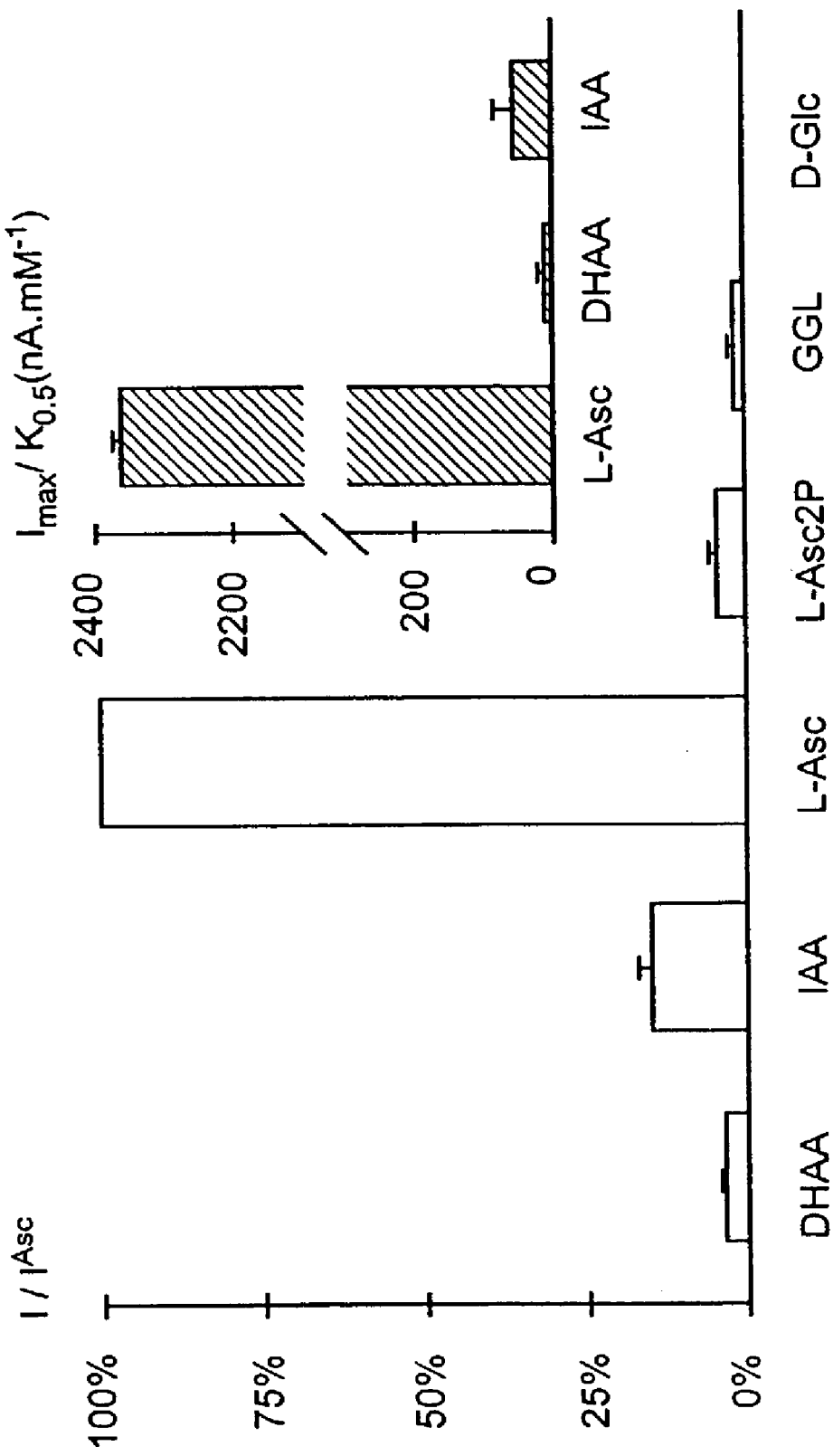
FIG. 9 demonstrates the substrate selectivity of human SVCT1.

Substrate selectivity of human SVCT1—No other substrate was found to be as effective in evoking a currrent as was L-ascorbic acid in oocytes expressing SVCT1. FIG. 9 illustrates currents evoked by test substrates (each applied at 500 µM in oocytes clamped at −50 mV) normalized to the L-ascorbic acid-evoked currents in the same oocytes (−114±20 nA, mean±SEM from eight oocytes). The test substrates were dehydroascorbic acid (DHAA); D-isoascorbic acid (IAA); L-ascorbic acid (L-Asc); L-ascorbic acid-2-phosphate (L-Asc2P); L-gulono-γ-lactone (GGL); and D-glucose (D-Glc).

The $K_{0.5}$ for L-ascorbic acid (based on evoked currents at −50 mV and at 100 mM Na$^+$) was 54±10 µM (mean±propagated SEM from 5 oocytes). D-isoascorbic acid evoked a current about 15% that of L-ascorbic acid (each at 500 µM). Higher D-isoascorbic acid concentrations evoked currents similar to those for L-ascorbic acid (i.e., these two substrates exhibited similar $I_{max}$), but the $K_{0.5}$ for D-isoascorbic acid (2.7±1.2 mM) was two orders of magnitude higher than that for L-ascorbic acid. Dehydroascorbic acid and L-ascorbic acid-2-phosphate were barely transported. As shown in the inset graph of FIG. 8, the substrate preference of SVCT1 was expressed as the $I_{max}/K_{0.5}$ ratios for the first three of these transported compounds, illustrating an exquisite preference for L-ascorbic acid. L-Gulono-γ-lactone (an intermediary metabolite in the synthesis of L-ascorbic acid from D-glucose in animals that can synthesize endogenous L-ascorbic acid) and D-glucose were both excluded. In addition, L-[$^{14}$C]ascorbic acid uptake was not significantly inhibited by a range of lactic acid, uric acid, succinic acid, oxalic acid, asprin, D-glucose, 2-deoxy-D-glucose, D-mannitol, D-ribose, L-ribose or D-fructose (data not shown). However, L-ascorbic acid-6-palmitate resulted in modest inhibition (20-30%), suggesting that it may be a substrate.

Phloretin was found to be a potent inhibitor of L-[$^{14}$C] ascorbic acid uptake (≈80% inhibition, data not shown) and of the L-ascorbic acid-evoked current (FIG. 8A). Phloretin also blocked a Na$^+$ "leak" current that could occur in the absence of L-ascorbic acid or other substrate; this was found to be as much as 10% of the L-ascorbic acid-evoked current, proportionately smaller than the Na$^+$ leak pathway found in the rat SVCT1.

Human SVCT1 is approximately 30% similar (at the amino-acid level) to the mouse yolk-sac permease-like protein mYspl1. mYspl1 was proposed to be a nucleobase transporter on the basis of weak sequence homology with prokaryotic nucleobase transporters (Guimarães et al., *Development* 121:3335-3346 (1995)). A range of nucleobases, nucleosides and nucleoties were therefore included in the search for additional substrates for SVCT1. Nonetheless, of the nucleobases (adenine, thymine, uracil), nucleosides (adenosine, 2-deoxyadenosine, uridine, guanosine, inosine), ribonucleotides (AMP, ADP, ATP, GTP, UTP) and deoxyribonucleotides (dATP, dGTP, dCTP, dTTP) we tested, none resulted in any significant inhibition of L-[$^{14}$C]ascorbic acid uptake in oocytes expressing SVCT1.

Figure 10:
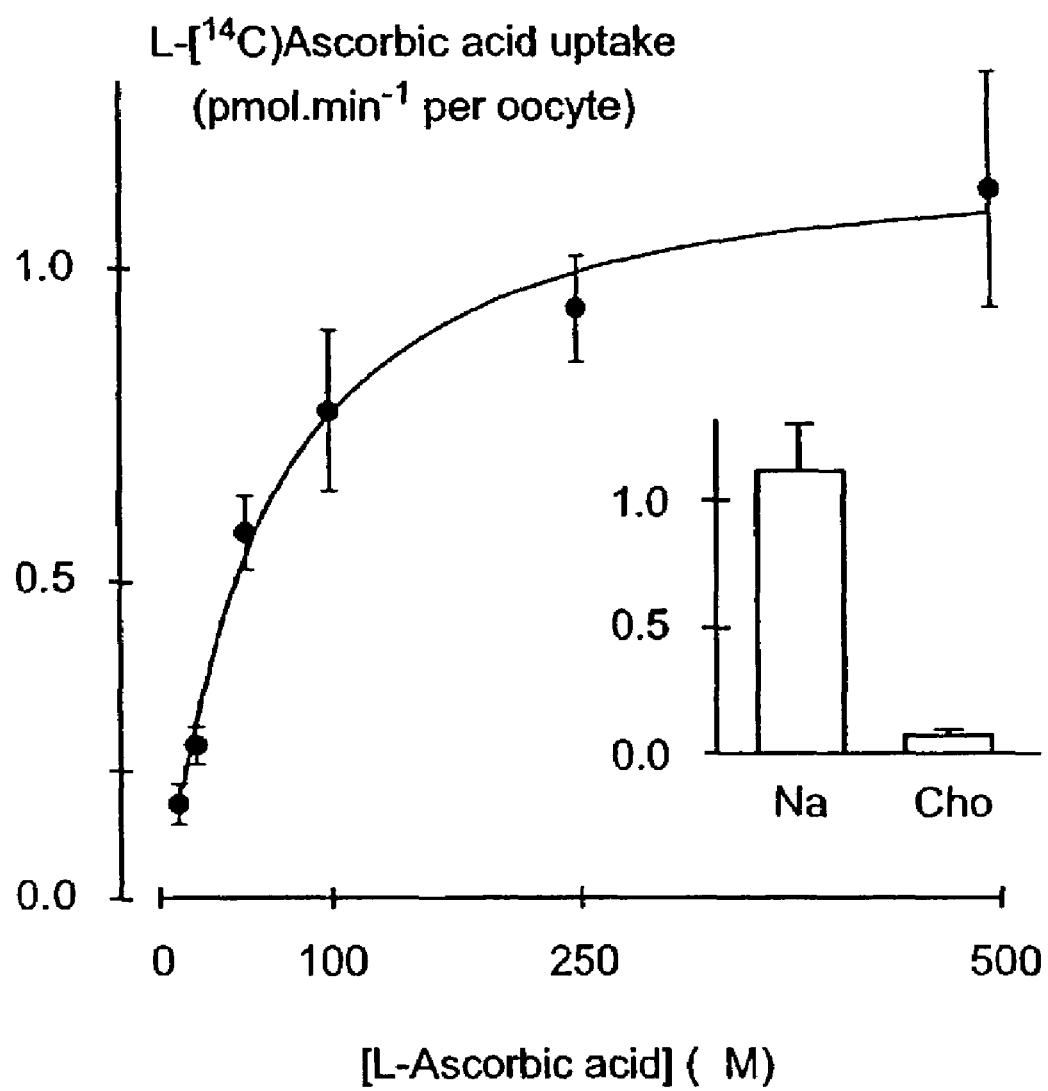
FIG. 10 graphically illustrates L-ascorbic acid transport activity associated with human SVCT2 based on isotope flux studies.

Identification of transport activity for human SVCT2—When expressed in oocytes, SVCT2 resulted in a 15-fold stimulation of L-[$^{14}$C]ascorbic acid uptake (1.2±0.1 pmol/min per oocyte) compared with control oocytes. Like SVCT1, SVCT2-mediated L-[$^{14}$C]ascorbic acid transport was saturable, with $K_{0.5}$ of 65 µM (FIG. 10), and 94% Na$^+$-dependent (FIG. 10, inset graph). Among a range of potential inhibitors tested, only saturating L-ascorbic acid inhibited the uptake of 100 µM L-[$^{14}$C]ascorbic acid. (The low SVCT2 expression levels in oocytes precluded detailed voltage-clamp analysis as performed for rat SVCT2.) Replacement of sodium ion by choline abolishes transport, confirming that SVCT2 is Na$^+$-coupled.

Tissue distribution of human SVCT1 and SVCT2—The tissue distribution of SVCT1 and SVCT2 was determined by Northern blot analysis of human tissues under high stringency conditions. Probing for SVCT1, transcripts of about 3 kb were detected in kidney, liver, small intestine, colon, ovary and prostate, with a weaker signal in pancreas. A transcript in thymus of around 9 kb may result from alternative splicing or may correspond to a closely-related gene product distinct from SVCT2. A 7.5-kb transcript was detected in most tissues probed for SVCT2, including brain, spleen, prostate, testis, ovary, placenta, and peripheral blood leukocytes.

Based on a survey of the frequency and tissue sources of closely-related EST clones, it is possible to predict additional tissues in which SVCT1 and SVCT2 may be expressed. These are shown in the following table:

TABLE 1

|  | Human | | Mouse | |
| --- | --- | --- | --- | --- |
|  | SVCT1 | SVCT2 | SVCT1 | SVCT2 |
| Tissue | | | | |
| Brain |  | $4^A$ |  |  |
| Retina |  | $15^B$ |  |  |
| Pineal gland |  | $1^C$ |  |  |
| Adipose tissue (white) |  | $1^D$ |  |  |
| Skin (melanocyte) |  | $4^E$ |  |  |
| Lymph node |  |  |  | $2^F$ |
| Germinal center B cells | $1^G$ |  |  |  |
| T cell |  | $1^H$ | $2^I$ |  |
| Mammary gland |  |  |  | $5^J$ |
| Uterus (during pregnancy) |  | $5^K$ |  |  |
| Human tumors | | | | |
| Kidney |  | $2^L$ |  |  |
| Uterus |  | $1^M$ |  |  |
| Prostatic neoplasia |  | $1^N$ |  |  |
| Parathyroid tumor |  | $5^O$ |  |  |
| Anaplastic oligodendroglioma |  | $2^P$ |  |  |
| Glioblastoma |  | $1^Q$ |  |  |
| Gessler Wilms tumor |  | $1^R$ |  |  |
| Pooled germ cell tumors |  | $2^S$ |  |  |
| Ovary |  | $1^T$ |  |  |

Corresponding EST database accession numbers are:
$^A$AA322234, AA323329, AA323374, AA984438;
$^B$H01519, H01625, R81499, R81742, T53720, T54313, W28570, W28623, AA000999, AA001558, AA012920, AA013005, AA013480, AA015699, AA021020;
$^C$AA364385;
$^D$AA302691;
$^E$H99366, N23756, N32463, N32511;
$^F$AA185385, AA210597;
$^G$AA811090;
$^H$A352785;
$^I$AA097984, AI550622;
$^J$AA472304, AA821651, AA9801311, AI465994, AI606903;
$^K$AA028023, AA028024, AA085766, AA128373, AI095660;
$^L$AI334656;
$^M$AI367693;
$^N$AA604857;
$^O$AA782627, AA854872, AI040896, AI056144, AI078653;
$^P$AI497603, AI582791;
$^Q$AI056441;
$^R$AA665698;
$^S$AA655944, AI206350;
$^T$AA075501.

Identification of SVCT1-related EST clones was limited to B lymphocytes of the germinal center as well as certain tumor cell types. However, numerous SVCT2-related EST clones were detected in several other tissues, suggesting that SVCT2 may also be expressed in pineal gland, retina, adipose tissue, skin, activated T-lymphocytes and uterus. Murine SVCT2 may also be expressed in mammary gland and lymph nodes.

3. Therapeutic Applications

Therapeutic applications involving modulation of the activity of vitamin C transporters include:

Cancer: It is well known that oxidative stress is a critical factor in cancer development. In some cancers, such as brain tumors, the cancer cells accumulate vitamin C as a free-radical scavenger to avoid damage by oxidative stress. Elevated levels of Vitamin C are also seen in lymphocytes of leukemia patients. Therefore, inhibition of the vitamin C transporters described herein may lead cancer therapies and preventative measures.

Brain tumors: In gliomas (i.e., astrocyte tumors, the most common brain tumors) oxidative stress is pronounced due to anaerobic glycolysis, and vitamin C accumulates to protect these cells. Vitamin C accumulation probably occurs through upregulation of SVCT2 in those cells. Therefore, inhibition of SVCT2 may lead to a therapeutic strategy to treat brain tumors and probably also other tumors.

Leukemia: Assignment of the gene encoding SVCT2 to the long arm of human chromosome 5, at band 5q31.2-31.3, within a region that is commonly deleted in malignant myeloid diseases raises the possibility that SVCT1 may play a role in tumor suppression. Indeed, in addition to its accepted role in antioxidation, there is growing interest in the potential use of L-ascorbic acid as an anticancer agent, a concept strengthened by the finding that this compound acid has a cytotoxic effect on leukemia cells in vitro.

Ischemia/stroke: In response to the anoxic state which occurs during ischemia, vitamin C is released from neurons to the extracellular space. As a consequence, when reoxygenation occurs following ischemia, free radicals will accumulate because the supply of intracellular vitamin C is no longer sufficient to scavenge the radicals. It is thought that people with enhanced brain vitamin C content enjoy improved protection against ischemia. Therefore, increased delivery of vitamin C by upregulation of the transporter proteins disclosed herein (i.e., increased transport across the choroid plexus and capillary endothelial cells, and/or increased absorption by the neurons) may represent an important therapeutic application.

During ischemia, there occurs a depletion of energy supply and a run-down of electrochemical ion gradients in neuronal cell membranes, which may result in reversed vitamin C transport (neuronal exit) by SVCT2. Depletion of vitamin C from neurons may exacerbate oxidative damage during the reoxygenation phase.

Eye: Increased accumulation of vitamin C by SVCT2 and SVCT1 in the cornea and tear fluid, respectively, protects the eye from damage due to ultraviolet radiation and oxidative stress. Studies indicate that both excessive and insufficient delivery of vitamin C to the eye lens may promote cataract formation. Therefore, depending on the situation, either inhibition or upregulation of SVCTs may be beneficial.

Vitamin C and dehydro-L-ascorbic acid (DHAA) cycling: Oxidation of vitamin C (e.g., as a result of scavenging of free radicals during oxidative stress), results in the formation of DHAA, which is toxic. Therefore, DHAA is kept at very low concentraion in normal human plasma. Certain cells such as astrocytes, lymphocytes, neutrophils and erythrocytes preferentially take up DHAA through facilitated glucose transporters of the GLUT-type. Once inside the cell, DHAA is reduced to vitamin C (either by direct chemical action of glutathione or by an enzymatic process that employs glutathinone and NADPH as reducing factors), and vitamin C is then released. In the brain, astrocytes regenerate vitamin C oxidized to DHAA due to neuronal activity, and return it back to neurons. In pathological situations, excessive oxidative stress may exceed the capacity of neurons and other cell types to regenerate oxidized vitamin C, which may lead to accumulation of toxic levels of DHAA.

Diabetes: SVCT2 is strongly expressed in the pancreas. Oxidative stress leads to accumulation of DHAA. Structurally, DHAA is similar to the diabetogenic agent alloxan, which destroys the pancreatic beta cells that produce insulin. Inhibition of SVCT2 specifically in the pancreas may limit DHM formation in the pancreas of diabetics and may help to protect the beta cells. Thus, therapeutic interventions of vitamin C transport and metabolism may lead to new treatment strategies for patients with diabetes.

Vitamin C in blood vessels and heart disease: Blood vessels require vitamin C in order to remain healthy. The vascular endothelium plays a key role in the local regulation of vascular tone by release of vasodilator substances such as nitric oxide (NO) and vasoconstrictor substances (i.e., thromboxane A2 and free radicals). NO plays an important role in basal and stimulated control of vascular tone in coronary arteries and coronary microcirculation, and regulation is altered by risk factors such as hypercholesterolemia, chronic smoking and hypertension. Endothelial dysfunction can cause myocardial ischemia and may be in part reversible by antioxidants such as vitamin C. Endothelial cells take up vitamin C in a sodium-dependent manner, possibly via SVCT2. Defective vitamin C metabolism in the vascular endothelium also leads to capillary fragility. Thus, therapeutic upregulation of SVCT2 in endothelial cells may be beneficial.

Therapeutic alteration of vitamin C homeostasis: Since plasma vitamin C is controlled at a fairly constant level (10-160 µM), whereas its concentration is at least 100 times higher in tissues (e.g., adrenal gland, thymus corpus luteum, retina, cornea) that depend on the vitamin, dietary vitamin C supplementation is probably not very effective in augmenting the cellular effects described above; this may explain the continuing controversy regarding the protective action of this vitamin in connection with the various noted pathologies. However, the ability to upregulate vitamin C transporters in specific tissues and cell types may allow a more effective increase in the supply of the vitamin to target tissues. Thus, this approach may lead to unique, highly promising and novel therapeutic applications.

Vitamin C levels inside the brain are under tight control and are compartmentalized. Vitamin C is delivered to the brain via SVCT2 in the choroid plexus and via the capillaries of the blood-brain barrier, which may also express SVCT2. Vitamin C enters neurons via SVCT2 which accumulate it at very high levels (up to 10 mM) for protection against reactive oxygen species produced during neuronal activity. Under normal conditions, asctrocytes accumulate vitamin C at much lower levels than neurons (~1 mM in astrocytes). Total brain tissue vitamin C levels are under hormonal control (i.e., regulation by circulating estrogen). Possibly, estrogen may directly affect the expression of SVCT2. Vitamin C levels in the brain also exhibit marked circadian patterns and variations are closely related to motor behavior through activation of certain glutamatergic pathways. This suggests novel therapeutic approaches for the treatment of insomnia and alteration of alertness. Vitamin C also acts as a neuromodulator of glutamatergic and dopaminergic neurotransmission. It is furthermore a co-factor in the synthesis of noradrenaline and many neuropeptides.

Therapeutic inhibitors and activators: As described above, phloretin has been demonstrated to inhibit SVCT1 and SVCT2.

Drug transport: Transport of drugs across epithelial barriers can be accomplished by linking a drug to a species transported by SVCT1 or SVCT2, thereby facilitating transport of the drug into cells expressing the transporter. For example, since the transporter SVCT1 is expressed in intestinal enterocytes, this strategy can be employed to facilitate oral administration of the drug. The drug linked to the transported species is absorbed intact into enterocytes, whereupon native enzymes inside the enterocyte or, following basolateral exit, in the blood or liver, cleave the drug from the transported species. Drugs that have proven amenable to an analogous approach using the intestinal peptide transporter PepT1 are acyclovir, the anti-viral, anti-herpes agent, and L-α-methyl-DOPA.

More specifically, drugs (possibly including antiviral drugs such as acyclovir) may be linked to L-ascorbic acid via ester-linkage, e.g., to the C5 or C6 hydroxyl group. Studies have shown that monosaccharide-conjugated drugs (such as acetaminophen) can be transported via the sodium glucose transporter SGLT1 in small intestine if the drugs are attached through and ether linkage to the C-1 of glucose, and that SGLT1 has spare space in its translocation pocket which can accommodate drugs if attached in the correct configuration; see Awazu et al. *Biochim. Biophys. Acta* 1381:340-346 (1998).

An important pathway for the metabolism of xenobiotics and cleavage of ester-linked prodrugs is catalyzed by the carboxylesterases, a family of enzymes that is involved in hydrolysis of chemical compounds, generally leading to detoxification. Several esterases have been purified, cloned, and characterized. Two forms, hydrolase A and hydrolase B, are present in liver microsomes in a number of species, including humans. These are also detected in extra-hepatic tissues. A third esterase, hydrolase S, is found in liver microsomes and serum, and may be a serum carboxylesterase secreted from the liver. See Yan et al., *J. Biol. Chem.* 270(32):19128-34 (1995). Thus, cleavage of these prodrug ester linkages may primarily occur in liver and blood, and not in epithelial cells of the intestine (enterocytes).

However, prodrugs may also include peptide bonds or ether linkage instead of ester bonds between the drug and the transported species. Peptide bonds may be hydrolized by specific peptidases that exist inside enterocytes.

Female infertility: It has been known for some time that vitamin C is essential for female fertility. Recent data has shown that vitamin C accumulates in maturing oocytes to high levels, and that this accumulation is compromised with aging. It is thought that the vitamin serves as a key antioxidant in eggs and early embryos. In women, a large component of the age-dependent loss of fertility is due to egg-dependent anomalies. In in vitro animal models, reactive oxygen species can create eggs of abnormal quality, similar to that seen in some infertile women, and infertility in some women may be due to inadequate levels of the antioxidant ascorbic acid. Understanding how eggs take up ascorbic acid and maintain their levels will facilitate understand this clinically relevant topic. Recent in situ hybridization data demonstrates that SVCT2 mRNA is strongly expressed in the rat ovary, in particular in thecal cells, granulosa cells, luteal cells and oocytes. SVCT2 expressed in the plasma membrane of these cells may play an important role in providing oocyte with appropriate supply of vitamin C. Similar to the adrenal medulla, SVCT2 also appears to be present in steroid producing cells of the ovary, i.e., thecal and luteal cells, where the vitamin C may be required as a cofactor for enzymatic reactions.

In addition, SVCT1 mRNA was also detected in the ovary where it may have similar functions as SVCT2. However, its cellular distribution in the ovary has not yet been determined.

Although the present invention has been described with reference to specific details, it is not intended that such details should be regarded as limitations upon the scope of the invention, except as and to the extent that they are included in the accompanying claims.

SEQ ID NO:1
Human SVCT1 DNA

```
   1 GTCATCCCCT CTTCTCCTCA GGAACTGCTC AAACCTGTGC CCCAAAGATG
  51 AGGGCCCAGG AGGACCTCGA GGGCCGGACA CAGCATGAAA CCACCAGGGA
 101 CCCCTCGACC CCGCTACCCA CAGAGCCTAA GTTTGACATG TTGTACAAGA
 151 TCGAGGACGT GCCACCTTGG TACCTGTGCA TCCTGCTGGG CTTCCAGCAC
 201 TACCTGACAT GCTTCAGTGG TACCATCGCC GTGCCCTTCC TGCTGGCTGA
 251 GGCGCTGTGT GTGGGCCACG ACCAGGACAT GGTTAGTCAG CTCATCGGCA
 301 CCATCTTCAC GTGCGTGGGC ATCACCACTC TCATCCAGAC CACCGTGGGC
 351 ATCCGGCTGC CGCTGTTCCA GGCCAGTGCC TTTGCATTTC TGGTTCCAGC
 401 CAAAGCCATA CTGGCTCTGG AGAGATGGAA ATGCCCCCG GAAGAGGAGA
 451 TCTACGGTAA CTGGAGTCTG CCCCTGAACA CCTCTCATAT TTGGCACCCA
 501 CGGATACGGG AGGTCCAGGG TGCAATCATG GTGTCCAGCG TGGTGGAGGT
 551 GGTGATTGGC CTGCTGGGGC TGCCTGGGGC CCTGCTCAAC TACATTGGGC
 601 CTCTCACAGT CACCCCCACT GTCTCCCTCA TTGGCCTTTC TGTCTTCCAA
 651 GCTGCTGGCG ACCGAGCTGG CTCCCACTGG GGCATCTCAG CTTGCTCCAT
 701 TCTCCTGATC ATCCTCTTCT CCCAGTACCT GCGCAACCTC ACCTTCCTGC
 751 TGCCTGTCTA CCGCTGGGGC AAGGGCCTCA CTCTCCTCCG CATCCAGATC
 801 TTCAAAATGT TTCCTATCAT GCTGGCCATC ATGACCGTGT GGCTGCTCTG
 851 CTATGTCCTG ACCTTGACAG ACGTGCTGCC CACAGACCCA AAAGCCTATG
 901 GCTTCCAGGC ACGAACCGAT GCCCGTGGTG ACATCATGGC TATTGCACCC
 951 TGGATCCGCA TCCCCTACCC CTGTCAGTGG GGCCTGCCCA CGGTGACTGC
1001 GGCTGCTGTC CTGGGAATGT TCAGCGCCAC TCTGGCAGGC ATCATTGAGT
1051 CCATCGGAGA TTACTACGCC TGTGCCCGCC TGGCTGGTGC ACCACCCCCT
1101 CCAGTACATG CTATCAACAG GGGCATCTTC ACCGAAGGCA TTTGCTGCAT
1151 CATCGCGGGG CTATTGGGCA CGGGCAACGG GTCCACCTCG TCCAGTCCCA
1201 ACATTGGCGT CCTGGGAATT ACCAAGGTGG GCAGCCGGCG CGTGGTGCAG
1251 TATGGTGCGG CTATCATGCT GGTCCTGGGC ACCATCGGCA AGTTCACGGC
1301 CCTCTTCGCC TCGCTCCCTG ACCCCATCCT GGGGGGCATG TTCTGCACTC
1351 TCTTTGGCAT GATTACAGCT GTGGGGCTGT CCAACCTGCA ATTTGTGGAC
1401 ATGAACTCCT CTCGCAACCT CTTCGTGCTG GGATTTTCCA TGTTCTTCGG
1451 GCTCACGCTG CCCAATTACC TGGAGTCCAA CCCTGGCGCC ATCAATACAG
1501 GCATTCTTGA AGTGGATCAG ATTCTGATTG TGCTGCTGAC CACGGAGATG
1551 TTTGTGGGCG GGTGCCTTGC TTTCATACTT GACAACACAG TGCCAGGGAG
1601 CCCAGAGGAG CGTGGTCTGA TACAGTGGAA AGCTGGGGCT CATGCCAACA
1651 GTGACATGTC TTCCAGCCTC AAGAGCTACG ATTTCCCCAT TGGGATGGGC
1701 ATAGTAAAAA GAATTACCTT TCTGAAATAC ATTCCTATCT GCCCAGTCTT
1751 CAAAGGATTT TCTTCAAGTT CAAAAGATCA GATTGCAATT CCAGAAGACA
1801 CTCCAGAAAA TACAGAAACT GCATCTGTGT GCACCAAGGT CTGAAAAATG
1851 ACTTCCAGGA AAGGAAGCAT GGTATATAAC AGGAAAAGAA AACTCATGG
1901 GGAACCAGAA GACCTAAGCC TGAAATCCCA GCCCTGCCCC TAACTAACTT
```

-continued

```
1951 CTGTGTAAAC TCAGATAAGT CACCTTTCTC TGGGATTCAA ATTTTTGCAT

2001 CAGTTAAAAA AAAAGGGGTG GGGGGGAATG GGCCAAAGTC TGAGTCTTAG

2051 AGACTTGTAC CAATGTTATG CTATGTCTCT AAATCTTTAC TCTCCTAAGT

2101 AGACTTGTCA GCATCTAGGA AGAACAGCTA GAAATTTTCC TCTGTGATAT

2151 TTTAGACTGC AAGTTGAAAA AAATAAAAAG AAATGAGGGC AGGTTCCAGG

2201 GCCTGAAATG TAGGTATGCT GCAAGGCTTT TACATTGAAT TTGACCCTAC

2251 ATCACTTCAA GACTAATGCA TAATATTAAA CATCATGTTG AAGAAATAAA

2301 AAAAAA
```

SEQ ID NO:2
Human SVCT2 DNA

```
   1 atgatgggta ttggtaagaa taccacatcc aaatcaatgg aggctggaag ttcaacagaa 61 ggcaaatacg aagacgaggc aaagcaccca gctttcttca ctcttccggt ggtgataaat 121 ggaggcgcca cctccagcgg tgagcaggac aatgaggaca ctgagctcat ggcgatctac 181 actacggaaa acggcattgc agaaaagagc tctctcgctg agaccctgga tagcactggc 241 agtctggacc cccagcgatc agacatgatt tataccatag aagatgttcc tccctggtac 301 ctgtgtatat ttctggggct acagcactac ctgacatgct tcagcggcac gatcgcagtg 361 cccttcctgt tggccgatgc catgtgtgtg ggtacgacc agtgggccac cagccagctc 421 attgggacca ttttcttctg tgtgggaatc actactttgc tacagacaac gtttggatgc 481 aggttacccc tgtttcagac cagtgctttt gcattttttgg ccctgctcg agccatcctg 541 tctttagata atggaaatg taacaccaca gatgtttcag ttgccaatgg aacagcagag 601 ctgttgcaca cagaacacat ctggtatccc cggatccgag agatccaggg ggccatcatc 661 atgtcctcac tgatagaagt agtcatcggc ctcctcggcc tgcctggggc tctactgaag 721 tacatcggtc ccttgaccat tacacccacg gtggccctaa ttggcctctc tggtttccag 781 gcagcggggg agagagccgg gaagcactgg ggcattgcca tgctgacaat attcctagta 841 ttactgtttt ctcaatacgc cagaaatgtt aaatttcctc tcccgattta taatccaag 901 aaaggatgga ctgcgtacaa gttacagctg ttcaaaatgt tccctatcat cctggccatc 961 ctggtatcct ggctgctctg cttcatcttc acggtgacag atgtcttccc tcccgacagc 1021 acaaagtatg gcttctatgc tcgcacagat gccaggcaag gcgtgcttct ggtagccccg 1081 tggtttaagg ttccatacc atttcagtgg ggactgccca ccgtgtctgc ggccggtgtc 1141 atcggcatgc tcagtgccgt ggtcgccagc atcatcgagt ctattggtga ctactacgcc 1201 tgtgcacggc tgtcctgtgc cccaccccc cccatccacg caataaacag gggaattttc 1261 gtggaaggcc tctcctgtgt tcttgatggc atatttggta ctgggaatgg ctctacttca 1321 tccagtccca acattggagt tttgggaatt acaaaggtcg gcagccgcc cgtgatacag 1381 tgcggagcag ccctcatgct cgctctgggc atgatcggga agttcagcgc cctctttgcg 1441 tcccttccgg atcctgtgct gggagccctg ttctgcacgc tctttggaat gatcacagct 1501 gttggcctct ctaacctgca gttcattgat ttaaattctt cccggaacct ctttgtgctt 1561 ggattttcga tcttctttgg gctcgtcctt ccaagttacc tcagacagaa ccctctggtc 1621 acagggataa caggaatcga tcaagtgttg aacgtccttc tcacaactgc tatgtttgta 1681 gggggctgtg tggcttttat cctggataac accatcccag gcactccaga ggaaagagga 1741 atccggaaat ggaagaaggg tgtgggcaaa gggaacaaat cactcgacgg catggagtcg
```

-continued

```
1801 tacaatttgc catttggcat gaacattata aaaaaataca gatgcttcag ctacttaccc
1861 atcagcccaa cctttgtggg ctacacatgg aaaggcctca ggaagagcga caacagccgg
1921 agttcagatg aagactccca ggccacggga tagcctttgc tgtgccctgt ggcctggccg
1981 cagtgaggca tgtatctgta gttccttgct
```

SEQ ID NO:3
Human SVCT1 Polypeptide

```
  1 MRAQEDLEGR TQHETTRDPS TPLPTEPKFD MLYKIEDVPP WYLCILLGFQ
 51 HYLTCFSGTI AVPFLLAEAL CVGHDQHMVS QLIGTIFTCV GITTLIQTTV
101 GIRLPLFQAS AFAFLVPAKA ILALERWKCF PEEEIYGNWS LPLNTSHIWH
151 PRIRDVQGAI MVSSVVEVVI GLLGLPGALL NYIGPLTVTP TVSLIGLSVF
201 QAAGDRAGSH WGISACSILL IILFSQYLRN LTFLLPVYRW GKGLTLLRIQ
251 IFKMFPIMLA IMTVWLLCYV LTLTEVLPTD PKAYGFQART DARGDIMAIA
301 PWIRIPYPCQ WGLPTVTAAA VLGMFSATLA GIIESIGDYY ACARLAGAPP
351 PPVHAINRGI FTEGICCIIA GLLGTGNGST SSSPNIGVLG ITKVGSRRVV
401 QYGAAIMLVL GTIGKFTALF ASLPDPILGG MFCTLFGMIT AVGLSNLQFV
451 DMNSSRNLFV LGFSMFFGLT LPNYLSPNPG AINTGILEVD QILIVLLTTE
501 MFVGGCLAFI LDNTVPGSPE ERGLIQWKAG AHANSDMSSS LKSYDFPIGM
551 GIVKRITFLK YIPICPVFKG FSSSSKDQIA IPEDTPENTE TASVCTKV
```

SEQ ID NO:4
Human SVCT2 Polypeptide

```
  1 MMGIGKNTTS KSMEAGSSTE GKYEDEAKHP AFFTLPVVIN GGATSSGEQD
 51 NEDTELMAIY TTENGIAEKS SLAETLDSTG SLDPQRSDMI YTIEDVPPWY
101 LCIFLGLQHY LTCFSGTIAV PFLLADANCV GYDQWATSQL IGTIFFCVGI
151 TTLLQTTFGC RLPLFQTSAF AFLAPARAIL SLDKWKCNTT DVSVANGTAE
201 LLHTEHIWYP RIREIQGAII MSSLIEVVIG LLGLPGALLK YIGPLTITPT
251 VALIGLSGFQ AAGERAGKHW GIAMLTIFLV LLFSQYARNV KFPLPIYKSK
301 KGWTAYKLQL FKMFPIILAI LVSWLLCFIF TVTDVFPPDS TKYGFYARTD
351 ARQGVLLVAP WFKVPYPFQW GLPTVSAAGV IGMLSAVVAS IIESIGDYYA
401 CARLSCAPPP PIHAINRGIF VEGLSCVLDG IFGTGNGSTS SSPNIGVLGI
451 TKVGSRRVIQ CGAALMLALG MIGKFSALFA SLPDPVLGAL FCTLFGMITA
501 VGLSNLQFID LNSSRNLFVL GFSIFFGLVL PSYLRQNPLV TGITGIDQVL
551 NVLLTTAMFV GGCVAFILDN TIPGTPEERG IRKWKKGVGK GNKSLDGMES
601 YNLPFGMNII KKYRCFSYLP ISPTFVGYTW KGLRKSDNSR SSDEDSQATG
```

SEQ ID NO:5
Rat SVCT1 DNA

```
  1 cagagatgaa agctcaggag daccccggga gctcaaagca gcatgaatgc ccagattcag
 61 cagggacttc caccagggac cagcaggcac ctttgcccgc ggagcccaag tttgacatgt
121 tgtacaagat tgaggacgtg ccaccatggt acctgtgtat cctgctgggc ttccagcatt
181 acctgacatg cttcagtggt accattgctg tgcccttcct cctggctgag cgcctgtgtg
241 tgggccgcga ccagcacatg atcagtcagc tcattggtac catcttcacc tgcgtgggta
301 tcaccactct cattcagact acagtgggca tccggctgcc gctgttccag gccagtgcct
361 ttgcgtttct ggttccagcc aaggctatcc tggccttgga gaggtggaag tgtcctccag
```

-continued

```
 421 aagaggagat ctacggtaac tggagtatgc ccctgaacac ctctcatatc tggcatcctc
 481 ggattcggga ggtccagggt gcaatcatgg tgtccagcgt ggtagaggtg gtgattgggc
 541 tgttggggct gcctgggcc ctgctcagct acattggacc tctcacagtc accccactg
 601 tctcccttat cggtctctct gttttccaag ctgctggcga ccgagctggc tcccattggg
 661 gcatttcggc ttgctccatt ctactgatcg tcctgttctc ccagtatcta cgcaacctca
 721 ccttcctgtt gcctgtttac cgatggggca agggtcttac tctcttccgc atccagatct
 781 ttaagatgtt tccgatcgtg ctggccatca tgaccgtgtg gctactctgc tatgtgctga
 841 ctctgacaga cgtgctgccc gcagatccca cagtctacgg tttccaggct cgaactgatg
 901 cccgagggga catcatggct atctctccct ggatccggat cccctaccca tgtcaatggg
 961 gcctacccac agtgaccgtg gctgcagttc tgggaatgtt cagcgccaca ctggcgggca
1021 tcatcgagtc catcggtgat tactatgcct gcgcccggtt ggctggagca ccaccccctc
1081 cagtccatgc tatcaacagg gggattttca ccgaaggcgt ctgctgcatc atcgctgggc
1141 tactgggcac aggcaacggg tccacctctt ccagccccaa catcggggtc tagggatta
1201 ccaaggtggg cagccgaaga gtcgtgcagt atggtgcagg tatcatgcta atcctggggg
1261 ccattggcaa attcacagct ctcttcgcct cactgccgga ccccatcctg ggagggatgt
1321 tctgcactct tttcggtatg atcaccgctg tgggactgtc caatctgcag tttgtggaca
1381 tgaactcctc ccgcaacctc tttgtattgg gattctccat gttcttcggc ctcacgctac
1441 ccaactacct ggattccaac ccaggtgcca tcaacacagg cgttcctgaa gtggatcaga
1501 tcctaactgt gctgctgacc acagagatgt tgttggtgg ctgtcttgct ttcatactgg
1561 acaacacagt accagggagc ccagaggaaa gaggtctgat acagtggaaa gccggggcac
1621 acgccaacag tgagacgctg gccagtctca agagctacga tttcccgttc gggatgggca
1681 tggtaaaaag gaccaccttt tttagataca tccccatctg cccagtcttc agaggattct
1741 ctaagacaga aaatcagcct gcagttctag aagacgctcc agacaacaca gaaactgggt
1801 ctgtgtgtac caaggtctga aactacctct atgaaaggag gcacggtgtg tatcaggaaa
1861 acaaactacc caggagacag aagacctgag ttggagatct cagctgtccc tattctaaat
1921 tcccatggaa gactggacag atcaccctct ctttgactcc attttcgtga cagcccaagt
1981 ctctaagtcc tcgggagacc tgtatttgca ctgctctgat tccttacttc cactttccta
2041 agcatgcatg tcaaggagga agagctggag aaaaaaaagg aaacccagag agattctagg
2101 gcttcatgta gacatgaaga tagggttaaa aacaaaccaa acaaaacccc ctgaattcca
2161 atgctatgta ttttaagacc aaaacagtat taaataatat actggaccaa taatttagat
2221 aagtttagat aagtattctc ccttcacaca gggaaaataa atttatactt tcagactagc
2281 tcagtgataa agatgtctat ttagaatgtt ccagaactgg gcttgacctt caacattaaa
2341 tatacagaaa taaaaaccct taagaggaaa aaaaagggg ttggggattt agctcagtgg
2401 tagagcgctt gcctagcaag cacaaggccc tgggttcggt ccccagctcc gggaaaaaaa
2461 aaaaaaaaaa aa
```

SEQ ID NO:6
Rat SVCT2 DNA

```
   1 cggcggcagg cactgcggcg cgagcggtgc gatcggcggg acgcgagccc agcgagctgc
  61 aggcaggtga taagcgatga cagtaatctg cgtctgagga tccagtgttc caggtgctaa
 121 aagctgcctc tggtcttaga cccctgcctt gcatacgcct tccctgcaag cactccaggc
```

-continued

```
 181 cacagtttgt aggctgctca gcctgccttg atgatgggtg tcggcaagaa cacatcaaag
 241 tcggtggagg ttgggggctc cacagaaggc aaatatgaag aggaggccaa gcgcccgat
 301 ttctttactc tcccggtggt gatcaatggt ggggccacgt ccagtggaga acaggacaat
 361 gaagacactg agctcatggc catctacacc acagagaatg gcattgcaga aaagagctct
 421 ctcgcagaga ccctggacag cactgggagc ctggatcccc agaggtcaga tatgatctac
 481 actatagaag acgttcctcc ctggtactta tgcatattcc tggggttgca gcactacctg
 541 acgtgtttca gtggcacaat cgcagtgccc tttttgctgg ctgatgccat gtgcgtgggg
 601 gatgaccagt gggccaccag ccagctcatc gggaccattt tcttctgcgt gggaatcact
 661 acattgctgc agacaacatt tggatgcagg ttaccctgt ttcaggccag tgcttttgca
 721 tttttggccc ctgctcgagc catcctgtct ttagataaat ggaaatgtaa caccacagag
 781 atcacagttg ccaacggaac ggcagagctg ttggaacaca tctggcaccc ccggatccaa
 841 gagatccagg gggctataat catgtcctca ctgatagaag tggtcattgg cctccttggc
 901 ctgcctgggg ctctgctgag gtatattgga cccttgacca tcacacccac cgtggccctc
 961 attggcctct ctggtttcca ggcagcagga gagcgagctg gaagcactg gggcattgcc
1021 atgctgacaa ttttcctagt gttactattc tcacaatatg ccagaaatgt taaatttcct
1081 ctcccaatct acaaatccaa gaaaggatgg acggcctaca agttacaact tttcaaaatg
1141 tttcctataa tcctggctat cctcgtgtcc tggctgctgt gcttcatctt cacggtgact
1201 gacgtcttcc cttccaacag caccgactat ggctactatg cacgcacaga tgccaggaag
1261 ggcgtacttc tggtagcccc atggtttaag gttccatacc catttcagtg ggggatgccc
1321 accgtctctg cagctggcgt cattggcatg ctcagtgctg tcgtagccag tatcattgag
1381 tccatcggcg actactatgc ctgcgccagg ctctcctgtg ccccaccacc tcctatacat
1441 gcaataaaca ggggtatttt tgtggagggt ctttcttgtg ttctcgatgg cgtatttggt
1501 accgggaatg gctctacctc ctccagtccc aatattggag ttttgggaat tacaaaggtt
1561 ggcagccgcc gagtgatcca gtatggtgca gctctcatgc tgggcttggg catgattggc
1621 aagttcagcg ccctcttcgc ctccctccca gaccctgtac tcggagccct cttctgcaca
1681 ctctttggaa tgatcacagc tgttggcctc tctaacctgc agttcattga cttgaattct
1741 tcccggaacc tatttgtgct tggatttcc atcttctttg gcttgttct tccaagttac
1801 ctcagacaaa accctctggt tacaggcata acaggcattg atcaagttct gaatgtcctt
1861 ctcaccactg ctatgttcgt cggaggctgt gtggcttta ttttggacaa caccatccca
1921 ggaaccccag aggaaagagg aatcaagaaa tggaagaagg gtgtgagcaa aggaaacaag
1981 tctcttgacg gcatggagtc ctataatttg ccatttggca tgaacattat taaaaaatac
2041 agatgcttca gctacctgcc tatcagccca acctttgcag gttacacatg gaaaggcttt
2101 gggaagagtg agaacaggcg gagttcagac aaagactccc aggccacagt atagcctttg
2161 ctgtgtcctg tggcctggcc acagtacggc atgcatctgt agttccttgc tgaataacaa
2221 gaagatatat gtttgtatat ctatctacat ggcatcctga cctcagagct aagacaggtt
2281 gcatatcact cttctgttgt gggtggtgat tatgtccaat atggtgtctc acttgtgtcc
2341 ttattgatcc cttacccgtt ttgtgtccat tgctggccat ggtcactgaa cttgaaatca
2401 cagtcctgcc attggagtgg gcatttggaa tctatagtgc cctgccttc aagtgctctc
2461 tttcttacaa gctgcttcga ggtctagggg tttctgcttc ttaaacacta tgtcccagtc
2521 ttcccatgtg acctcagcct gaaccctgtg agacctcct ctggccaggg gccactggtg
```

```
2581 tccttacttt gttgtgattc tattatcctt gatagcccag gagcctactg acctgactga 2641 gaataatgac atgtctgtcc tgtgaccaga tatgagtgtg cataaggtcc tgtatagctg 2701 tgactggggg agctctggtt aggagattga cagggagtag aacgatcctg agtcagtggg 2761 attctcaacc atgctccccc ctcgtcaccc tggacccatc tgggccagca cagttcatac 2821 tagtctcttt ctggccgaga caccctattt ggcattttca ctgctggctg gtgtgatggg 2881 tgttagagtg cccacaggta gtctgtgggt gtcttggctc tgctgccctg tatttgcgtg 2941 tgtttattc ctatttaatg ttattgacta tagcggattt ttgaaatcag tgttttccgt 3001 gtgaacttcc aaccttgcat cctgttcctt ggcctgtact ctttactcca ttgagaaaag 3061 aaccagcgtc tgtaaaagct gtgggtgcca tcagggaagc t
```

SEQ ID NO:7
Rat SVCT1 Polypeptide

MKAQEDPGSSKQHECPDSAGTSTRDQQAPLPAEPKFDMLYKIED

VPPWYLCILLGFQHYLTCFSGTIAVPFLLAEALCVGRDQHMISQLIGTIFTCVGITTL

IQTTVGIRLPLFQASAFAFLVPAKAILALERWKCPPEEEIYGNWSMPLNTSHIWHPRI

REVQGAIMVSSVVEVVIGLLGLPGALLSYIGPLTVTPTVSLIGLSVFQAAGDRAGSHW

GISACSILLIVLFSQYLRNLTFLLPVYRWGKGLTLFRIQIFKMFPIVLAIMTVWLLCY

VLTLTDVLPADPTVYGFQARTDARGDIMAISPWIRIPYPCQWGLPTVTVAAVLGMFSA

TLAGIIESIGDYYACARLAGAPPPPVHAINRGIFTEGVCCIIAGLLGTGNGSTSSSPN

IGVLGITKVGSRRVVQYGAGIMLILGAIGKFTALFASLPDPILGGMFCTLFGMITAVG

LSNLQFVDMNSSRNLFVLGFSMFFGLTLPNYLDSNPGAINTGVPEVDQILTVLLTTEM

FVGGCLAFILDNTVPGSPEERGLTQWKAGAHANSETLASLKSYDFPFGMGMVKRTTFF

RYIPICPVFRGFSKTENQPAVLEDAPDNTETGSVCTKV

SEQ ID NO:8
Rat SVCT2 Polypeptide

MAIYTTENGIAEKSSLAETLDSTGSLDPQRSDMIYTIEDVPPWY

LCIFLGLQHYLTCFSGTIAVPFLLADAMCVGDDQWATSQLIGTIFFCVGITTLLQTTF

GCRLPLFQASAFAFLAPARAILSLDKWKCNTTEITVANGTAELLEHIWHPRIQEIQGA

IIMSSLIEVVIGLLGLPGALLRYIGPLTITPTVALIGLSGFQAAGERAGKHWGIAMLT

IFLVLLFSQYARNVKFPLPIYKSKKGWTAYKLQLFKMFPIILAILVSWLLCFIFTVTD

VFPSNSTDYGYYARTDARKGVLLVAPWFKVPYPFQWGMPTVSAAGVIGMLSAVVASII

ESIGDYYACARLSCAPPPPIHAINRGIFVEGLSCVLDGVFGTGNGSTSSSPNIGVLGI

TKVGSRRVIQYGAALMLGLGMIGKFSALFASLPDPVLGALFCTLFGMITAVGLSNLQF

IDLNSSRNLFVLGFSIFFGLVLPSYLRQNPLVTGITGIDQVLNVLLTTAMFVGGCVAF

ILDNTIPGTPEERGIKKWKKGVSKGNKSLDGMESYNLPFGMNIIKKYRCFSYLPISPT

FAGYTWKGFGKSENRRSSDKDSQATV

---

What is claimed is:

1. A method of transporting vitamin C across a membrane, the method comprising the steps of:
   a. expressing a protein comprising an amino-acid sequence having at least 90% homology to SEQ ID NO: 4, wherein the protein exhibits sodium dependence and transports vitamin C across membranes;
   b. integrating the protein within a membrane; and
   c. contacting the membrane, under conditions favoring vitamin C transport, with vitamin C, thereby resulting in transmembrane transport of vitamin C.

2. The method of claim 1, wherein the membrane comprises a lipid bilayer.

3. The method of claim 1, wherein the protein is integrated by transforming an isolated cell with a nucleic acid encoding the protein, thereby causing expression of the protein within the cell and integration of the protein in a membrane of the cell.

4. The method of claim 1, wherein the protein corresponds at least to conserved regions of the sequence of SEQ ID NO: 4.

5. The method of claim 3, wherein the cell is transformed by transfection with the nucleic acid.

6. The method of claim 3, wherein the cell is derived from kidney, uterus, liver, brain, ovary, skin, endocrine, exocrine, retina, pineal gland, adipose, mammary gland, lymph node, brain, or intestine tissue.

7. The method of claim 3, wherein the cell is a neuron, astrocyte, cancer cell, epithelial cell, enterocyte, colon cell, prostate cell, endothelial cell, neuroendocrine cell, corneal epithelial cell, pigmented ciliary epithelial cell, T cell, melanocyte, or osteoblast.

* * * * *

SEQUENCE LISTING

<160> NUMBER OF SEQ ID NOS: 14

<210> SEQ ID NO 1
<211> LENGTH: 2306
<212> TYPE: DNA

<213> ORGANISM: Homo sapiens

<400> SEQUENCE: 1

| | | | | | |
|---|---|---|---|---|---|
| gtcatcccct | cttctcctca | ggaactgctc | aaacctgtgc | cccaaagatg | agggcccagg | 60 |
| aggacctcga | gggccggaca | cagcatgaaa | ccaccaggga | cccctcgacc | ccgctaccca | 120 |
| cagagcctaa | gtttgacatg | ttgtacaaga | tcgaggacgt | gccaccttgg | tacctgtgca | 180 |
| tcctgctggg | cttccagcac | tacctgacat | gcttcagtgg | taccatcgcc | gtgcccttcc | 240 |
| tgctggctga | ggcgctgtgt | gtgggccacg | accagcacat | ggttagtcag | ctcatcggca | 300 |
| ccatcttcac | gtgcgtgggc | atcaccactc | tcatccagac | caccgtgggc | atccggctgc | 360 |
| cgctgttcca | ggccagtgcc | tttgcatttc | tggttccagc | caaagccata | ctggctctgg | 420 |
| agagatggaa | atgcccccg | gaagaggaga | tctacggtaa | ctggagtctg | ccctgaaca | 480 |
| cctctcatat | ttggcaccca | cggatacggg | aggtccaggg | tgcaatcatg | gtgtccagcg | 540 |
| tggtggaggt | ggtgattggc | ctgctggggc | tgcctgggc | cctgctcaac | tacattgggc | 600 |
| ctctcacagt | caccccact | gtctccctca | ttggcctttc | tgtcttccaa | gctgctggcg | 660 |
| accgagctgg | ctcccactgg | ggcatctcag | cttgctccat | tctcctgatc | atcctcttct | 720 |
| cccagtacct | gcgcaacctc | accttcctgc | tgcctgtcta | ccgctggggc | aagggcctca | 780 |
| ctctcctccg | catccagatc | ttcaaaatgt | ttcctatcat | gctggccatc | atgaccgtgt | 840 |
| ggctgctctg | ctatgtcctg | accttgacag | acgtgctgcc | cacagaccca | aaagcctatg | 900 |
| gcttccaggc | acgaaccgat | gcccgtggtg | acatcatggc | tattgcaccc | tggatccgca | 960 |
| tcccctaccc | ctgtcagtgg | ggcctgccca | cggtgactgc | ggctgctgtc | ctgggaatgt | 1020 |
| tcagcgccac | tctggcaggc | atcattgagt | ccatcggaga | ttactacgcc | tgtgcccgcc | 1080 |
| tggctggtgc | accaccccct | ccagtacatg | ctatcaacag | gggcatcttc | accgaaggca | 1140 |
| tttgctgcat | catcgcgggg | ctattgggca | cgggcaacgg | gtccacctcg | tccagtccca | 1200 |
| acattggcgt | cctgggaatt | accaaggtgg | gcagccggcg | cgtggtgcag | tatggtgcgg | 1260 |
| ctatcatgct | ggtcctgggc | accatcggca | agttcacggc | cctcttcgcc | tcgctccctg | 1320 |
| accccatcct | gggggcatg | ttctgcactc | tctttggcat | gattacagct | gtggggctgt | 1380 |
| ccaacctgca | atttgtggac | atgaactcct | ctcgcaacct | cttcgtgctg | ggattttcca | 1440 |
| tgttcttcgg | gctcacgctg | cccaattacc | tggagtccaa | ccctggcgcc | atcaatacag | 1500 |
| gcattcttga | agtggatcag | attctgattg | tgctgctgac | cacggagatg | tttgtgggcg | 1560 |
| ggtgccttgc | tttcatactt | gacaacacag | tgccagggag | cccagaggag | cgtggtctga | 1620 |
| tacagtggaa | agctggggct | catgccaaca | gtgacatgtc | ttccagcctc | aagagctacg | 1680 |
| atttccccat | tgggatgggc | atagtaaaaa | gaattacctt | tctgaaatac | attcctatct | 1740 |
| gcccagtctt | caaaggattt | tcttcaagtt | caaaagatca | gattgcaatt | ccagaagaca | 1800 |
| ctccagaaaa | tacagaaact | gcatctgtgt | gcaccaaggt | ctgaaaaatg | acttccagga | 1860 |
| aaggaagcat | ggtatataac | aggaaaagaa | aactacatgg | ggaaccagaa | gacctaagcc | 1920 |
| tgaaatccca | gccctgcccc | taactaactt | ctgtgtaaac | tcagataagt | cacctttctc | 1980 |
| tgggattcaa | attttttgcat | cagttaaaaa | aaagggtg | ggggaatg | ggccaaagtc | 2040 |
| tgagtcttag | agacttgtac | caatgttatg | ctatgtctct | aaatcttac | tctcctaagt | 2100 |
| agacttgtca | gcatctagga | agaacagcta | gaaattttcc | tctgtgatat | tttagactgc | 2160 |
| aagttgaaaa | aaataaaaag | aaatgagggc | aggttccagg | gcctgaaatg | taggtatgct | 2220 |
| gcaaggcttt | tacattgaat | ttgaccctac | atcacttcaa | gactaatgca | taatattaaa | 2280 |

```
catcatgttg aagaaataaa aaaaaa                                          2306

<210> SEQ ID NO 2
<211> LENGTH: 2010
<212> TYPE: DNA
<213> ORGANISM: Homo sapiens

<400> SEQUENCE: 2
atgatgggta ttggtaagaa taccacatcc aaatcaatgg aggctggaag ttcaacagaa      60
ggcaaatacg aagacgaggc aaagcaccca gctttcttca ctcttccggt ggtgataaat     120
ggaggcgcca cctccagcgg tgagcaggac aatgaggaca ctgagctcat ggcgatctac     180
actacggaaa acggcattgc agaaaagagc tctctcgctg agaccctgga tagcactggc     240
agtctggacc cccagcgatc agacatgatt tataccatag aagatgttcc tccctggtac     300
ctgtgtatat ttctggggct acagcactac ctgacatgct tcagcggcac gatcgcagtg     360
cccttcctgt tggccgatgc catgtgtgtg gggtacgacc agtgggccac cagccagctc     420
attgggacca ttttcttctg tgtgggaatc actactttgc tacagacaac gtttggatgc     480
aggttacccc tgtttcagac cagtgctttt gcattttggg ccctgctcg agccatcctg      540 tctttagata aatggaaatg taacaccaca gatgtttcag ttgccaatgg aacagcagag     600
ctgttgcaca cagaacacat ctggtatccc cggatccgag agatccaggg ggccatcatc     660
atgtcctcac tgatagaagt agtcatcggc ctcctcggcc tgcctggggc tctactgaag     720
tacatcggtc ccttgaccat tacacccacg gtggccctaa ttggcctctc tggtttccag     780
gcagcggggg agagagccgg gaagcactgg ggcattgcca tgctgacaat attcctagta     840
ttactgtttt ctcaatacgc cagaaatgtt aaatttcctc tcccgattta taatccaag      900 aaaggatgga ctgcgtacaa gttacagctg ttcaaaatgt tccctatcat cctggccatc     960
ctggtatcct ggctgctctg cttcatcttc acggtgacag atgtcttccc tcccgacagc    1020
acaaagtatg gcttctatgc tcgcacagat gccaggcaag gcgtgcttct ggtagccccg    1080
tggtttaagg ttccataccc atttcagtgg ggactgccca ccgtgtctgc ggccggtgtc    1140
atcggcatgc tcagtgccgt ggtcgccagc atcatcgagt ctattggtga ctactacgcc    1200
tgtgcacggc tgtcctgtgc cccaccccc cccatccacg caataaacag gggaattttc    1260
gtggaaggcc tctcctgtgt tcttgatggc atatttggta ctgggaatgg ctctacttca    1320
tccagtccca acattggagt tttgggaatt acaaaggtcg gcagccgccg cgtgatacag    1380
tgcggagcag ccctcatgct cgctctgggc atgatcggga agttcagcgc cctctttgcg    1440
tcccttccgg atcctgtgct gggagccctg ttctgcacgc tctttggaat gatcacagct    1500
gttggcctct ctaacctgca gttcattgat ttaaattctt cccggaacct ctttgtgctt    1560
ggattttcga tcttctttgg gctcgtcctt ccaagttacc tcagacagaa ccctctggtc    1620
acagggataa caggaatcga tcaagtgttg aacgtccttc tcacaactgc tatgtttgta    1680
gggggctgtg tggctttat cctggataac accatcccag gcactccaga ggaaagagga    1740
atccggaaat ggaagaaggg tgtgggcaaa gggaacaaat cactcgacgg catggagtcg    1800
tacaatttgc catttggcat gaacattata aaaaaataca gatgcttcag ctacttaccc    1860
atcagcccaa cctttgtggg ctacacatgg aaaggcctca ggaagagcga caacagccgg    1920
agttcagatg aagactccca ggccacggga tagccttgc tgtgccctgt ggcctggccg    1980
cagtgaggca tgtatctgta gttccttgct                                    2010
```

<210> SEQ ID NO 3
<211> LENGTH: 598
<212> TYPE: PRT
<213> ORGANISM: Homo sapiens

<400> SEQUENCE: 3

Met Arg Ala Gln Glu Asp Leu Glu Gly Arg Thr Gln His Glu Thr Thr
1               5                   10                  15

Arg Asp Pro Ser Thr Pro Leu Pro Thr Glu Pro Lys Phe Asp Met Leu
            20                  25                  30

Tyr Lys Ile Glu Asp Val Pro Pro Trp Tyr Leu Cys Ile Leu Leu Gly
        35                  40                  45

Phe Gln His Tyr Leu Thr Cys Phe Ser Gly Thr Ile Ala Val Pro Phe
    50                  55                  60

Leu Leu Ala Glu Ala Leu Cys Val Gly His Asp Gln His Met Val Ser
65                  70                  75                  80

Gln Leu Ile Gly Thr Ile Phe Thr Cys Val Gly Ile Thr Thr Leu Ile
                85                  90                  95

Gln Thr Thr Val Gly Ile Arg Leu Pro Leu Phe Gln Ala Ser Ala Phe
            100                 105                 110

Ala Phe Leu Val Pro Ala Lys Ala Ile Leu Ala Leu Glu Arg Trp Lys
        115                 120                 125

Cys Pro Pro Glu Glu Glu Ile Tyr Gly Asn Trp Ser Leu Pro Leu Asn
    130                 135                 140

Thr Ser His Ile Trp His Pro Arg Ile Arg Asp Val Gln Gly Ala Ile
145                 150                 155                 160

Met Val Ser Ser Val Val Glu Val Val Ile Gly Leu Leu Gly Leu Pro
                165                 170                 175

Gly Ala Leu Leu Asn Tyr Ile Gly Pro Leu Thr Val Thr Pro Thr Val
            180                 185                 190

Ser Leu Ile Gly Leu Ser Val Phe Gln Ala Ala Gly Asp Arg Ala Gly
        195                 200                 205

Ser His Trp Gly Ile Ser Ala Cys Ser Ile Leu Leu Ile Ile Leu Phe
    210                 215                 220

Ser Gln Tyr Leu Arg Asn Leu Thr Phe Leu Leu Pro Val Tyr Arg Trp
225                 230                 235                 240

Gly Lys Gly Leu Thr Leu Leu Arg Ile Gln Ile Phe Lys Met Phe Pro
                245                 250                 255

Ile Met Leu Ala Ile Met Thr Val Trp Leu Leu Cys Tyr Val Leu Thr
            260                 265                 270

Leu Thr Glu Val Leu Pro Thr Asp Pro Lys Ala Tyr Gly Phe Gln Ala
        275                 280                 285

Arg Thr Asp Ala Arg Gly Asp Ile Met Ala Ile Ala Pro Trp Ile Arg
    290                 295                 300

Ile Pro Tyr Pro Cys Gln Trp Gly Leu Pro Thr Val Thr Ala Ala Ala
305                 310                 315                 320

Val Leu Gly Met Phe Ser Ala Thr Leu Ala Gly Ile Ile Glu Ser Ile
                325                 330                 335

Gly Asp Tyr Tyr Ala Cys Ala Arg Leu Ala Gly Ala Pro Pro Pro Pro
            340                 345                 350

Val His Ala Ile Asn Arg Gly Ile Phe Thr Glu Gly Ile Cys Cys Ile
        355                 360                 365

Ile Ala Gly Leu Leu Gly Thr Gly Asn Gly Ser Thr Ser Ser Ser Pro
    370                 375                 380

```
Asn Ile Gly Val Leu Gly Ile Thr Lys Val Gly Ser Arg Arg Val Val
385                 390                 395                 400

Gln Tyr Gly Ala Ala Ile Met Leu Val Leu Gly Thr Ile Gly Lys Phe
                405                 410                 415

Thr Ala Leu Phe Ala Ser Leu Pro Asp Pro Ile Leu Gly Gly Met Phe
            420                 425                 430

Cys Thr Leu Phe Gly Met Ile Thr Ala Val Gly Leu Ser Asn Leu Gln
            435                 440                 445

Phe Val Asp Met Asn Ser Ser Arg Asn Leu Phe Val Leu Gly Phe Ser
        450                 455                 460

Met Phe Phe Gly Leu Thr Leu Pro Asn Tyr Leu Ser Pro Asn Pro Gly
465                 470                 475                 480

Ala Ile Asn Thr Gly Ile Leu Glu Val Asp Gln Ile Leu Ile Val Leu
                485                 490                 495

Leu Thr Thr Glu Met Phe Val Gly Gly Cys Leu Ala Phe Ile Leu Asp
            500                 505                 510

Asn Thr Val Pro Gly Ser Pro Glu Glu Arg Gly Leu Ile Gln Trp Lys
        515                 520                 525

Ala Gly Ala His Ala Asn Ser Asp Met Ser Ser Ser Leu Lys Ser Tyr
530                 535                 540

Asp Phe Pro Ile Gly Met Gly Ile Val Lys Arg Ile Thr Phe Leu Lys
545                 550                 555                 560

Tyr Ile Pro Ile Cys Pro Val Phe Lys Gly Phe Ser Ser Ser Ser Lys
                565                 570                 575

Asp Gln Ile Ala Ile Pro Glu Asp Thr Pro Glu Asn Thr Glu Thr Ala
            580                 585                 590

Ser Val Cys Thr Lys Val
            595

<210> SEQ ID NO 4
<211> LENGTH: 650
<212> TYPE: PRT
<213> ORGANISM: Homo sapiens

<400> SEQUENCE: 4

Met Met Gly Ile Gly Lys Asn Thr Thr Ser Lys Ser Met Glu Ala Gly
1               5                   10                  15

Ser Ser Thr Glu Gly Lys Tyr Glu Asp Glu Ala Lys His Pro Ala Phe
                20                  25                  30

Phe Thr Leu Pro Val Val Ile Asn Gly Gly Ala Thr Ser Ser Gly Glu
            35                  40                  45

Gln Asp Asn Glu Asp Thr Glu Leu Met Ala Ile Tyr Thr Thr Glu Asn
        50                  55                  60

Gly Ile Ala Glu Lys Ser Ser Leu Ala Glu Thr Leu Asp Ser Thr Gly
65                  70                  75                  80

Ser Leu Asp Pro Gln Arg Ser Asp Met Ile Tyr Thr Ile Glu Asp Val
                85                  90                  95

Pro Pro Trp Tyr Leu Cys Ile Phe Leu Gly Leu Gln His Tyr Leu Thr
                100                 105                 110

Cys Phe Ser Gly Thr Ile Ala Val Pro Phe Leu Leu Ala Asp Ala Met
            115                 120                 125

Cys Val Gly Tyr Asp Gln Trp Ala Thr Ser Gln Leu Ile Gly Thr Ile
        130                 135                 140

Phe Phe Cys Val Gly Ile Thr Thr Leu Leu Gln Thr Thr Phe Gly Cys
```

-continued

```
            145                 150                 155                 160
Arg Leu Pro Leu Phe Gln Thr Ser Ala Phe Ala Phe Leu Ala Pro Ala
                165                 170                 175
Arg Ala Ile Leu Ser Leu Asp Lys Trp Lys Cys Asn Thr Thr Asp Val
                180                 185                 190
Ser Val Ala Asn Gly Thr Ala Glu Leu Leu His Thr Glu His Ile Trp
                195                 200                 205
Tyr Pro Arg Ile Arg Glu Ile Gln Gly Ala Ile Ile Met Ser Ser Leu
                210                 215                 220
Ile Glu Val Val Ile Gly Leu Leu Gly Leu Pro Gly Ala Leu Leu Lys
225                 230                 235                 240
Tyr Ile Gly Pro Leu Thr Ile Thr Pro Thr Val Ala Leu Ile Gly Leu
                245                 250                 255
Ser Gly Phe Gln Ala Ala Gly Glu Arg Ala Gly Lys His Trp Gly Ile
                260                 265                 270
Ala Met Leu Thr Ile Phe Leu Val Leu Leu Phe Ser Gln Tyr Ala Arg
                275                 280                 285
Asn Val Lys Phe Pro Leu Pro Ile Tyr Lys Ser Lys Lys Gly Trp Thr
                290                 295                 300
Ala Tyr Lys Leu Gln Leu Phe Lys Met Phe Pro Ile Ile Leu Ala Ile
305                 310                 315                 320
Leu Val Ser Trp Leu Leu Cys Phe Ile Phe Thr Val Thr Asp Val Phe
                325                 330                 335
Pro Pro Asp Ser Thr Lys Tyr Gly Phe Tyr Ala Arg Thr Asp Ala Arg
                340                 345                 350
Gln Gly Val Leu Leu Val Ala Pro Trp Phe Lys Val Pro Tyr Pro Phe
                355                 360                 365
Gln Trp Gly Leu Pro Thr Val Ser Ala Ala Gly Val Ile Gly Met Leu
                370                 375                 380
Ser Ala Val Val Ala Ser Ile Ile Glu Ser Ile Gly Asp Tyr Tyr Ala
385                 390                 395                 400
Cys Ala Arg Leu Ser Cys Ala Pro Pro Pro Ile His Ala Ile Asn
                405                 410                 415
Arg Gly Ile Phe Val Glu Gly Leu Ser Cys Val Leu Asp Gly Ile Phe
                420                 425                 430
Gly Thr Gly Asn Gly Ser Thr Ser Ser Ser Pro Asn Ile Gly Val Leu
                435                 440                 445
Gly Ile Thr Lys Val Gly Ser Arg Arg Val Ile Gln Cys Gly Ala Ala
                450                 455                 460
Leu Met Leu Ala Leu Gly Met Ile Gly Lys Phe Ser Ala Leu Phe Ala
465                 470                 475                 480
Ser Leu Pro Asp Pro Val Leu Gly Ala Leu Phe Cys Thr Leu Phe Gly
                485                 490                 495
Met Ile Thr Ala Val Gly Leu Ser Asn Leu Gln Phe Ile Asp Leu Asn
                500                 505                 510
Ser Ser Arg Asn Leu Phe Val Leu Gly Phe Ser Ile Phe Phe Gly Leu
                515                 520                 525
Val Leu Pro Ser Tyr Leu Arg Gln Asn Pro Leu Val Thr Gly Ile Thr
                530                 535                 540
Gly Ile Asp Gln Val Leu Asn Val Leu Leu Thr Thr Ala Met Phe Val
545                 550                 555                 560
Gly Gly Cys Val Ala Phe Ile Leu Asp Asn Thr Ile Pro Gly Thr Pro
                565                 570                 575
```

-continued

```
Glu Glu Arg Gly Ile Arg Lys Trp Lys Lys Gly Val Gly Lys Gly Asn
            580                 585                 590

Lys Ser Leu Asp Gly Met Glu Ser Tyr Asn Leu Pro Phe Gly Met Asn
            595                 600                 605

Ile Ile Lys Lys Tyr Arg Cys Phe Ser Tyr Leu Pro Ile Ser Pro Thr
            610                 615                 620

Phe Val Gly Tyr Thr Trp Lys Gly Leu Arg Lys Ser Asp Asn Ser Arg
625                 630                 635                 640

Ser Ser Asp Glu Asp Ser Gln Ala Thr Gly
                645                 650

<210> SEQ ID NO 5
<211> LENGTH: 2472
<212> TYPE: DNA
<213> ORGANISM: Rattus rattus

<400> SEQUENCE: 5
```

| | |
|---|---|
| cagagatgaa agctcaggag gaccccggga gctcaaagca gcatgaatgc ccagattcag | 60 |
| cagggacttc caccagggac cagcaggcac ctttgcccgc ggagcccaag tttgacatgt | 120 |
| tgtacaagat tgaggacgtg ccaccatggt acctgtgtat cctgctgggc ttccagcatt | 180 |
| acctgacatg cttcagtggt accattgctg tgcccttcct cctggctgag cgctgtgtg | 240 |
| tgggccgcga ccagcacatg atcagtcagc tcattggtac catcttcacc tgcgtgggta | 300 |
| tcaccactct cattcagact acagtgggca tccggctgcc gctgttccag gccagtgcct | 360 |
| ttgcgtttct ggttccagcc aaggctatcc tggccttgga gaggtggaag tgtcctccag | 420 |
| aagaggagat ctacggtaac tggagtatgc ccctgaacac ctctcatatc tggcatcctc | 480 |
| ggattcggga ggtccagggt gcaatcatgg tgtccagcgt ggtagaggtg gtgattgggc | 540 |
| tgttggggct gctgggggcc ctgctcagct acattggacc tctcacagtc accccccactg | 600 |
| tctcccttat cggtctctct gttttccaag ctgctggcga ccgagctggc tcccattggg | 660 |
| gcatttcggc ttgctccatt ctactgatcg tcctgttctc ccagtatcta cgcaacctca | 720 |
| ccttcctgtt gcctgtttac cgatggggca agggtcttac tctcttccgc atccagatct | 780 |
| ttaagatgtt tccgatcgtg ctggccatca tgaccgtgtg ctactctgc tatgtgctga | 840 |
| ctctgacaga cgtgctgccc gcagatccca cagtctacgg tttccaggct cgaactgatg | 900 |
| cccgagggga catcatggct atctctccct ggatccggat ccctacccca tgtcaatggg | 960 |
| gcctacccac agtgaccgtg gctgcagttc tgggaatgtt cagcgccaca ctggcgggca | 1020 |
| tcatcgagtc catcggtgat tactatgcct gcgcccggtt ggctggagca ccacccccctc | 1080 |
| cagtccatgc tatcaacagg gggattttca ccgaaggcgc tgctgcatc atcgctgggc | 1140 |
| tactgggcac aggcaacggg tccacctctt ccagccccaa catcggggtc ctaggattta | 1200 |
| ccaaggtggg cagccgaaga gtcgtgcagt atggtgcagg tatcatgcta atcctggggg | 1260 |
| ccattggcaa attcacagct ctcttcgcct cactgccgga ccccatcctg ggaggatgt | 1320 |
| tctgcactct tttcggtatg atcaccgctg tgggactgtc caatctgcag tttgtggaca | 1380 |
| tgaactcctc ccgcaaccte tttgtattgg gattctccat gttcttcggc ctcacgctac | 1440 |
| ccaactacct ggattccaac ccaggtgcca tcaacacagg cgttcctgaa gtggatcaga | 1500 |
| tcctaactgt gctgctgacc acagagatgt tgttggtgg ctgtcttgct ttcatactgg | 1560 |
| acaacacagt accagggagc ccagaggaaa gaggtctgat acagtggaaa gccggggcac | 1620 |
| acgccaacag tgagacgctg gccagtctca agagctacga tttcccgttc gggatgggca | 1680 |

```
tggtaaaaag gaccacctttt tttagataca tccccatctg cccagtcttc agaggattct    1740
ctaagacaga aaatcagcct gcagttctag aagacgctcc agacaacaca gaaactgggt    1800
ctgtgtgtac caaggtctga aactacctct atgaaggag gcacggtgtg tatcaggaaa    1860
acaaactacc caggagacag aagacctgag ttggagatct cagctgtccc tattctaaat    1920
tcccatggaa gactgacag atcaccctct ctttgactcc attttcgtga cagcccaagt    1980
ctctaagtcc tcgggagacc tgtatttgca ctgctctgat tccttacttc cactttccta    2040
agcatgcatg tcaaggagga agagctggag aaaaaaagg aaacccagag agattctagg    2100
gcttcatgta gacatgaaga tagggttaaa acaaaccaa acaaaacccc ctgaattcca    2160
atgctatgta ttttaagacc aaaacagtat taaataatat actggaccaa taatttagat    2220
aagtttagat aagtattctc ccttcacaca gggaaaataa atttatactt tcagactagc    2280
tcagtgataa agatgtctat ttagaatgtt ccagaactgg gcttgacctt caacattaaa    2340
tatacagaaa taaaaaccct taagaggaaa aaaaagggg ttggggattt agctcagtgg    2400
tagagcgctt gcctagcaag cacaaggccc tgggttcggt ccccagctcc gggaaaaaaa    2460
aaaaaaaaaa aa                                                          2472

<210> SEQ ID NO 6
<211> LENGTH: 3101
<212> TYPE: DNA
<213> ORGANISM: Rattus rattus

<400> SEQUENCE: 6
cggcggcagg cactgcggcg cgagcggtgc gatcggcggg acgcgagccc agcgagctgc      60
aggcaggtga taagcgatga cagtaatctg cgtctgagga tccagtgttc caggtgctaa     120
aagctgcctc tggtcttaga cccctgcctt gcatacgcct tccctgcaag cactccaggc     180
cacagtttgt aggctgctca gcctgccttg atgatgggtg tcggcaagaa cacatcaaag     240
tcggtggagg ttgggggctc cacagaaggc aaatatgaag aggaggccaa gcgccccgat     300
ttctttactc tcccggtggt gatcaatggt ggggccacgt ccagtggaga acaggacaat     360
gaagacactg agctcatggc catctacacc acagagaatg gcattgcaga aagagctct     420 ctcgcagaga ccctggacag cactgggagc ctggatcccc agaggtcaga tatgatctac     480
actatagaag acgttcctcc ctggtactta tgcatattcc tggggttgca gcactacctg     540
acgtgtttca gtggcacaat cgcagtgccc tttttgctgg ctgatgccat gtgcgtgggg     600
gatgaccagt gggccaccag ccagctcatc gggaccattt tcttctgcgt gggaatcact     660
acattgctgc agacaacatt tggatgcagg ttacccctgt tcaggccag tgcttttgca     720 tttttggccc ctgctcgagc catcctgtct ttagataaat ggaaatgtaa caccacagag    780
atcacagttg ccaacggaac ggcagagctg ttggaacaca tctggcaccc ccggatccaa    840
gagatccagg gggctataat catgtcctca ctgatagaag tggtcattgg cctccttggc    900
ctgcctgggg ctctgctgag gtatattgga cccttgacca tcacacccac cgtggccctc    960
attggcctct ctggtttcca ggcagcagga gagcgagctg ggaagcactg ggcacattgcc   1020 atgctgacaa ttttcctagt gttactattc tcacaatatg ccagaaatgt taaatttcct   1080
ctcccaatct acaaatccaa gaaaggatgg acggcctaca agttacaact tttcaaaatg   1140
tttcctataa tcctggctat cctcgtgtcc tggctgctgt gcttcatctt cacggtgact   1200
gacgtcttcc cttccaacag caccgactat ggctactatg cacgcacaga tgccaggaag   1260
```

```
ggcgtacttc tggtagcccc atggtttaag gttccatacc catttcagtg ggggatgccc    1320
accgtctctg cagctggcgt cattggcatg ctcagtgctg tcgtagccag tatcattgag    1380
tccatcggcg actactatgc ctgcgccagg ctctcctgtg ccccaccacc tcctatacat    1440
gcaataaaca ggggtatttt tgtggagggt cttttcttgtg ttctcgatgg cgtatttggt    1500
```

```
ggcgtacttc tggtagcccc atggtttaag gttccatacc catttcagtg ggggatgccc    1320
accgtctctg cagctggcgt cattggcatg ctcagtgctg tcgtagccag tatcattgag    1380
tccatcggcg actactatgc ctgcgccagg ctctcctgtg ccccaccacc tcctatacat    1440
gcaataaaca ggggtatttt tgtggagggt cttttcttgtg ttctcgatgg cgtatttggt    1500
accgggaatg gctctacctc ctccagtccc aatattggag ttttgggaat tacaaaggtt    1560
ggcagccgcc gagtgatcca gtatggtgca gctctcatgc tgggcttggg catgattggc    1620
aagttcagcg ccctcttcgc ctccctccca gaccctgtac tcggagccct cttctgcaca    1680
ctctttggaa tgatcacagc tgttggcctc tctaacctgc agttcattga cttgaattct    1740
tcccggaacc tatttgtgct tggatttttcc atcttctttg ggcttgttct tccaagttac    1800
ctcagacaaa accctctggt tacaggcata acaggcattg atcaagttct gaatgtcctt    1860
ctcaccactg ctatgttcgt cggaggctgt gtggctttta ttttggacaa caccatccca    1920
ggaaccccag aggaaagagg aatcaagaaa tggaagaagg gtgtgagcaa aggaaacaag    1980
tctcttgacg gcatggagtc ctataatttg ccatttggca tgaacattat taaaaaatac    2040
agatgcttca gctacctgcc tatcagccca acctttgcag gttacacatg gaaaggcttt    2100
gggaagagtg agaacaggcg gagttcagac aaagactccc aggccacagt atagcctttg    2160
ctgtgtcctg tggcctggcc acagtacggc atgcatctgt agttccttgc tgaataacaa    2220
gaagatatat gtttgtatat ctatctacat ggcatcctga cctcagagct aagacaggtt    2280
gcatatcact cttctgttgt gggtggtgat tatgtccaat atggtgtctc acttgtgtcc    2340
ttattgatcc cttacccgtt ttgtgtccat tgctggccat ggtcactgaa cttgaaatca    2400
cagtcctgcc attggagtgg gcatttggaa tctatagtgc cctgccttc aagtgctctc    2460
tttcttacaa gctgcttcga ggtctagggg tttctgcttc ttaaacacta tgtcccagtc    2520
ttcccatgtg acctcagcct gaaccctgtg gagacctcct ctggccaggg gccactggtg    2580
tccttacttt gttgtgattc tattatcctt gatagcccag gagcctactg acctgactga    2640
gaataatgac atgtctgtcc tgtgaccaga tatgagtgtg cataaggtcc tgtatagctg    2700
tgactggggg agctctggtt aggagattga cagggagtag aacgatcctg agtcagtggg    2760
attctcaacc atgctccccc ctcgtcaccc tggacccatc tgggccagca cagttcatac    2820
tagtctcttt ctggccgaga caccctattt ggcattttca ctgctggctg gtgtgatggg    2880
tgttagagtg cccacaggta gtctgtgggt gtcttggctc tgctgccctg tatttgcgtg    2940
tgttttattc ctatttaatg ttattgacta tagcggattt ttgaaatcag tgttttccgt    3000
gtgaacttcc aaccttgcat cctgttcctt ggcctgtact ctttactcca ttgagaaaag    3060
aaccagcgtc tgtaaaagct gtgggtgcca tcagggaagc t                        3101
```

<210> SEQ ID NO 7
<211> LENGTH: 604
<212> TYPE: PRT
<213> ORGANISM: Rattus rattus

<400> SEQUENCE: 7

Met Lys Ala Gln Glu Asp Pro Gly Ser Ser Lys Gln His Glu Cys Pro
1               5                   10                  15

Asp Ser Ala Gly Thr Ser Thr Arg Asp Gln Gln Ala Pro Leu Pro Ala
            20                  25                  30

Glu Pro Lys Phe Asp Met Leu Tyr Lys Ile Glu Asp Val Pro Pro Trp
        35                  40                  45

```
Tyr Leu Cys Ile Leu Leu Gly Phe Gln His Tyr Leu Thr Cys Phe Ser
        50                  55                  60

Gly Thr Ile Ala Val Pro Phe Leu Leu Ala Glu Ala Leu Cys Val Gly
65                  70                  75                  80

Arg Asp Gln His Met Ile Ser Gln Leu Ile Gly Thr Ile Phe Thr Cys
                    85                  90                  95

Val Gly Ile Thr Thr Leu Ile Gln Thr Thr Val Gly Ile Arg Leu Pro
                100                 105                 110

Leu Phe Gln Ala Ser Ala Phe Ala Phe Leu Val Pro Ala Lys Ala Ile
            115                 120                 125

Leu Ala Leu Glu Arg Trp Lys Cys Pro Glu Glu Glu Ile Tyr Gly
        130                 135                 140

Asn Trp Ser Met Pro Leu Asn Thr Ser His Ile Trp His Pro Arg Ile
145                 150                 155                 160

Arg Glu Val Gln Gly Ala Ile Met Val Ser Ser Val Glu Val Val
                165                 170                 175

Ile Gly Leu Leu Gly Leu Pro Gly Ala Leu Leu Ser Tyr Ile Gly Pro
                180                 185                 190

Leu Thr Val Thr Pro Thr Val Ser Leu Ile Gly Leu Ser Val Phe Gln
            195                 200                 205

Ala Ala Gly Asp Arg Ala Gly Ser His Trp Gly Ile Ser Ala Cys Ser
210                 215                 220

Ile Leu Leu Ile Val Leu Phe Ser Gln Tyr Leu Arg Asn Leu Thr Phe
225                 230                 235                 240

Leu Leu Pro Val Tyr Arg Trp Gly Lys Gly Leu Thr Leu Phe Arg Ile
                245                 250                 255

Gln Ile Phe Lys Met Phe Pro Ile Val Leu Ala Ile Met Thr Val Trp
            260                 265                 270

Leu Leu Cys Tyr Val Leu Thr Leu Thr Asp Val Leu Pro Ala Asp Pro
        275                 280                 285

Thr Val Tyr Gly Phe Gln Ala Arg Thr Asp Ala Arg Gly Asp Ile Met
        290                 295                 300

Ala Ile Ser Pro Trp Ile Arg Ile Pro Tyr Pro Cys Gln Trp Gly Leu
305                 310                 315                 320

Pro Thr Val Thr Val Ala Ala Val Leu Gly Met Phe Ser Ala Thr Leu
                325                 330                 335

Ala Gly Ile Ile Glu Ser Ile Gly Asp Tyr Tyr Ala Cys Ala Arg Leu
            340                 345                 350

Ala Gly Ala Pro Pro Pro Val His Ala Ile Asn Arg Gly Ile Phe
        355                 360                 365

Thr Glu Gly Val Cys Cys Ile Ile Ala Gly Leu Leu Gly Thr Gly Asn
        370                 375                 380

Gly Ser Thr Ser Ser Ser Pro Asn Ile Gly Val Leu Gly Ile Thr Lys
385                 390                 395                 400

Val Gly Ser Arg Arg Val Val Gln Tyr Gly Ala Gly Ile Met Leu Ile
                405                 410                 415

Leu Gly Ala Ile Gly Lys Phe Thr Ala Leu Phe Ala Ser Leu Pro Asp
            420                 425                 430

Pro Ile Leu Gly Gly Met Phe Cys Thr Leu Phe Gly Met Ile Thr Ala
        435                 440                 445

Val Gly Leu Ser Asn Leu Gln Phe Val Asp Met Asn Ser Ser Arg Asn
450                 455                 460

Leu Phe Val Leu Gly Phe Ser Met Phe Phe Gly Leu Thr Leu Pro Asn
```

-continued

```
                465                 470                 475                 480
Tyr Leu Asp Ser Asn Pro Gly Ala Ile Asn Thr Gly Val Pro Glu Val
                    485                 490                 495

Asp Gln Ile Leu Thr Val Leu Leu Thr Thr Glu Met Phe Val Gly Gly
                500                 505                 510

Cys Leu Ala Phe Ile Leu Asp Asn Thr Val Pro Gly Ser Pro Glu Glu
                515                 520                 525

Arg Gly Leu Ile Gln Trp Lys Ala Gly Ala His Ala Asn Ser Glu Thr
                530                 535                 540

Leu Ala Ser Leu Lys Ser Tyr Asp Phe Pro Phe Gly Met Gly Met Val
545                 550                 555                 560

Lys Arg Thr Thr Phe Phe Arg Tyr Ile Pro Ile Cys Pro Val Phe Arg
                    565                 570                 575

Gly Phe Ser Lys Thr Glu Asn Gln Pro Ala Val Leu Glu Asp Ala Pro
                580                 585                 590

Asp Asn Thr Glu Thr Gly Ser Val Cys Thr Lys Val
                595                 600
```

<210> SEQ ID NO 8
<211> LENGTH: 592
<212> TYPE: PRT
<213> ORGANISM: Rattus rattus

<400> SEQUENCE: 8

```
Met Ala Ile Tyr Thr Thr Glu Asn Gly Ile Ala Glu Lys Ser Ser Leu
1               5                   10                  15

Ala Glu Thr Leu Asp Ser Thr Gly Ser Leu Asp Pro Gln Arg Ser Asp
                20                  25                  30

Met Ile Tyr Thr Ile Glu Asp Val Pro Pro Trp Tyr Leu Cys Ile Phe
                35                  40                  45

Leu Gly Leu Gln His Tyr Leu Thr Cys Phe Ser Gly Thr Ile Ala Val
                50                  55                  60

Pro Phe Leu Leu Ala Asp Ala Met Cys Val Gly Asp Asp Gln Trp Ala
65                  70                  75                  80

Thr Ser Gln Leu Ile Gly Thr Ile Phe Phe Cys Val Gly Ile Thr Thr
                    85                  90                  95

Leu Leu Gln Thr Thr Phe Gly Cys Arg Leu Pro Leu Phe Gln Ala Ser
                100                 105                 110

Ala Phe Ala Phe Leu Ala Pro Ala Arg Ala Ile Leu Ser Leu Asp Lys
                115                 120                 125

Trp Lys Cys Asn Thr Thr Glu Ile Thr Val Ala Asn Gly Thr Ala Glu
                130                 135                 140

Leu Leu Glu His Ile Trp His Pro Arg Ile Gln Glu Ile Gln Gly Ala
145                 150                 155                 160

Ile Ile Met Ser Ser Leu Ile Glu Val Val Ile Gly Leu Leu Gly Leu
                    165                 170                 175

Pro Gly Ala Leu Leu Arg Tyr Ile Gly Pro Leu Thr Ile Thr Pro Thr
                180                 185                 190

Val Ala Leu Ile Gly Leu Ser Gly Phe Gln Ala Ala Gly Glu Arg Ala
                195                 200                 205

Gly Lys His Trp Gly Ile Ala Met Leu Thr Ile Phe Leu Val Leu Leu
                210                 215                 220

Phe Ser Gln Tyr Ala Arg Asn Val Lys Phe Pro Leu Pro Ile Tyr Lys
225                 230                 235                 240
```

```
Ser Lys Lys Gly Trp Thr Ala Tyr Lys Leu Gln Leu Phe Lys Met Phe
            245                 250                 255

Pro Ile Ile Leu Ala Ile Leu Val Ser Trp Leu Leu Cys Phe Ile Phe
            260                 265                 270

Thr Val Thr Asp Val Phe Pro Ser Asn Ser Thr Asp Tyr Gly Tyr Tyr
            275                 280                 285

Ala Arg Thr Asp Ala Arg Lys Gly Val Leu Leu Val Ala Pro Trp Phe
            290                 295                 300

Lys Val Pro Tyr Pro Phe Gln Trp Gly Met Pro Thr Val Ser Ala Ala
305                 310                 315                 320

Gly Val Ile Gly Met Leu Ser Ala Val Val Ala Ser Ile Ile Glu Ser
            325                 330                 335

Ile Gly Asp Tyr Tyr Ala Cys Ala Arg Leu Ser Cys Ala Pro Pro Pro
            340                 345                 350

Pro Ile His Ala Ile Asn Arg Gly Ile Phe Val Glu Gly Leu Ser Cys
            355                 360                 365

Val Leu Asp Gly Val Phe Gly Thr Gly Asn Gly Ser Thr Ser Ser Ser
            370                 375                 380

Pro Asn Ile Gly Val Leu Gly Ile Thr Lys Val Gly Ser Arg Arg Val
385                 390                 395                 400

Ile Gln Tyr Gly Ala Ala Leu Met Leu Gly Leu Gly Met Ile Gly Lys
            405                 410                 415

Phe Ser Ala Leu Phe Ala Ser Leu Pro Asp Pro Val Leu Gly Ala Leu
            420                 425                 430

Phe Cys Thr Leu Phe Gly Met Ile Thr Ala Val Gly Leu Ser Asn Leu
            435                 440                 445

Gln Phe Ile Asp Leu Asn Ser Ser Arg Asn Leu Phe Val Leu Gly Phe
            450                 455                 460

Ser Ile Phe Phe Gly Leu Val Leu Pro Ser Tyr Leu Arg Gln Asn Pro
465                 470                 475                 480

Leu Val Thr Gly Ile Thr Gly Ile Asp Gln Val Leu Asn Val Leu Leu
            485                 490                 495

Thr Thr Ala Met Phe Val Gly Gly Cys Val Ala Phe Ile Leu Asp Asn
            500                 505                 510

Thr Ile Pro Gly Thr Pro Glu Glu Arg Gly Ile Lys Lys Trp Lys Lys
            515                 520                 525

Gly Val Ser Lys Gly Asn Lys Ser Leu Asp Gly Met Glu Ser Tyr Asn
530                 535                 540

Leu Pro Phe Gly Met Asn Ile Ile Lys Lys Tyr Arg Cys Phe Ser Tyr
545                 550                 555                 560

Leu Pro Ile Ser Pro Thr Phe Ala Gly Tyr Thr Trp Lys Gly Phe Gly
            565                 570                 575

Lys Ser Glu Asn Arg Arg Ser Asp Lys Asp Ser Gln Ala Thr Val
            580                 585                 590

<210> SEQ ID NO 9
<211> LENGTH: 605
<212> TYPE: PRT
<213> ORGANISM: Mus sp.

<400> SEQUENCE: 9

Met Lys Thr Pro Glu Asp Pro Gly Ser Pro Lys Gln His Glu Val Val
1               5                   10                  15

Asp Ser Ala Gly Thr Ser Thr Arg Asp Arg Gln Ala Pro Leu Pro Thr
            20                  25                  30
```

-continued

```
Glu Pro Lys Phe Asp Met Leu Tyr Lys Ile Glu Asp Val Pro Pro Trp
             35                  40                  45
Tyr Leu Cys Ile Leu Leu Gly Phe Gln His Tyr Leu Thr Cys Phe Ser
 50                  55                  60
Gly Thr Ile Ala Val Pro Phe Leu Leu Ala Glu Ala Leu Cys Val Gly
 65                  70                  75                  80
Arg Asp Gln His Met Val Ser Gln Leu Ile Gly Thr Ile Phe Thr Cys
                 85                  90                  95
Val Gly Ile Thr Thr Leu Ile Gln Thr Thr Val Gly Ile Arg Leu Pro
                100                 105                 110
Leu Phe Gln Ala Ser Ala Phe Ala Phe Leu Val Pro Ala Lys Ser Ile
            115                 120                 125
Leu Ala Leu Glu Arg Trp Lys Cys Pro Ser Glu Glu Ile Tyr Gly
            130                 135                 140
Asn Trp Ser Met Pro Leu Asn Thr Ser His Ile Trp His Pro Arg Ile
145                 150                 155                 160
Arg Glu Val Gln Gly Ala Ile Met Val Ser Ser Met Val Glu Val Val
                165                 170                 175
Ile Gly Leu Met Gly Leu Pro Gly Ala Leu Leu Ser Tyr Ile Gly Pro
                180                 185                 190
Leu Thr Val Thr Pro Thr Val Ser Leu Ile Gly Leu Tyr Val Phe Gln
            195                 200                 205
Ala Ala Gly Asp Arg Ala Gly Ser His Trp Gly Ile Ser Ala Cys Ser
            210                 215                 220
Ile Leu Leu Ile Val Leu Phe Ser Gln Tyr Leu Arg Asn Leu Thr Phe
225                 230                 235                 240
Leu Leu Pro Val Tyr Arg Trp Gly Lys Gly Leu Thr Leu Phe Arg Val
                245                 250                 255
Gln Ile Phe Lys Met Phe Pro Ile Val Leu Ala Ile Met Thr Val Trp
                260                 265                 270
Leu Leu Cys Tyr Val Leu Thr Leu Thr Asp Val Leu Pro Ala Asp Pro
            275                 280                 285
Thr Val Tyr Gly Phe Gln Ala Arg Thr Asp Ala Arg Gly Asp Ile Met
            290                 295                 300
Ala Ile Ser Pro Trp Ile Arg Ile Pro Tyr Pro Cys Gln Trp Gly Leu
305                 310                 315                 320
Pro Thr Val Thr Val Ala Ala Val Leu Gly Met Phe Ser Ala Thr Leu
                325                 330                 335
Ala Gly Ile Ile Glu Ser Ile Gly Asp Tyr Tyr Ala Cys Ala Arg Leu
            340                 345                 350
Ala Gly Ala Pro Pro Pro Val His Ala Ile Asn Arg Gly Ile Phe
            355                 360                 365
Thr Glu Gly Ile Cys Cys Ile Ile Ala Gly Leu Leu Gly Thr Gly Asn
            370                 375                 380
Gly Ser Thr Ser Ser Ser Pro Asn Ile Gly Val Leu Gly Ile Thr Lys
385                 390                 395                 400
Val Gly Ser Arg Arg Val Val Gln Tyr Gly Ala Gly Ile Met Leu Ile
                405                 410                 415
Leu Gly Ala Ile Gly Lys Phe Thr Ala Leu Phe Ala Ser Leu Pro Asp
            420                 425                 430
Pro Ile Leu Gly Gly Met Phe Cys Thr Leu Phe Gly Met Ile Thr Ala
            435                 440                 445
```

```
Val Gly Leu Ser Asn Leu Gln Phe Val Asp Met Asn Ser Ser Arg Asn
    450                 455                 460
Leu Phe Val Leu Gly Phe Ser Met Phe Phe Gly Leu Thr Leu Pro Asn
465                 470                 475                 480
Tyr Leu Asp Ser Asn Pro Gly Ala Ile Asn Thr Gly Ile Pro Glu Val
                485                 490                 495
Asp Gln Ile Leu Thr Val Leu Leu Thr Thr Glu Met Phe Val Gly Gly
            500                 505                 510
Cys Leu Ala Phe Ile Leu Asp Asn Thr Val Pro Gly Ser Pro Glu Glu
        515                 520                 525
Arg Gly Leu Ile Gln Trp Lys Ala Gly Ala His Ala Asn Ser Glu Thr
    530                 535                 540
Ser Ala Ser Leu Lys Ser Tyr Asp Phe Pro Phe Gly Met Gly Met Val
545                 550                 555                 560
Lys Arg Thr Thr Phe Phe Arg Tyr Ile Pro Ile Cys Pro Val Phe Arg
                565                 570                 575
Gly Phe Ser Lys Lys Thr Gln Asn Gln Pro Pro Val Leu Glu Asp Thr
            580                 585                 590
Pro Asp Asn Ile Glu Thr Gly Ser Val Cys Thr Lys Val
        595                 600                 605

<210> SEQ ID NO 10
<211> LENGTH: 650
<212> TYPE: PRT
<213> ORGANISM: Sus sp.

<400> SEQUENCE: 10

Met Met Gly Ile Gly Lys Thr Ser Ser Lys Ser Met Glu Ala Gly Ser
1               5                   10                  15
Ser Ala Glu Gly Lys Tyr Glu Asp Glu Ala Lys His Pro Thr Phe Phe
                20                  25                  30
Thr Leu Pro Val Val Thr Asn Gly Gly Ala Thr Ser Ser Gly Glu Gln
            35                  40                  45
Asp Asn Glu Asp Thr Glu Leu Met Ala Ile Tyr Thr Thr Glu Asn Gly
        50                  55                  60
Ile Ala Glu Lys Ser Ser Leu Ala Glu Thr Leu Asp Ser Thr Gly Ser
65                  70                  75                  80
Leu Asp Pro Gln Arg Ser Asp Met Ile Tyr Thr Ile Glu Asp Val Pro
                85                  90                  95
Pro Trp Tyr Leu Cys Ile Phe Leu Gly Leu Gln His Tyr Leu Thr Cys
            100                 105                 110
Phe Ser Gly Thr Ile Ala Val Pro Phe Leu Leu Ala Asp Ala Met Cys
        115                 120                 125
Val Gly Tyr Asp Gln Trp Ala Thr Ser Gln Leu Ile Gly Thr Ile Leu
    130                 135                 140
Phe Cys Val Gly Ile Thr Thr Leu Leu Gln Thr Thr Phe Gly Cys Arg
145                 150                 155                 160
Leu Pro Leu Phe Gln Ala Ser Ala Phe Ala Phe Leu Ala Pro Ala Arg
                165                 170                 175
Ala Ile Leu Ser Leu Asp Lys Trp Lys Cys Asn Thr Thr Asp Val Ser
            180                 185                 190
Val Ala Asn Gly Thr Thr Glu Leu Leu His Thr Glu His Met Trp Tyr
        195                 200                 205
Pro Arg Ile Arg Glu Ile Gln Gly Ala Ile Ile Met Ser Ser Leu Ile
    210                 215                 220
```

-continued

```
Glu Val Val Ile Gly Leu Leu Gly Leu Pro Gly Ala Leu Leu Lys Tyr
225                 230                 235                 240

Ile Gly Pro Leu Gly Ile Thr Pro Thr Val Ala Leu Ile Gly Leu Ser
                245                 250                 255

Gly Phe Gln Ala Ala Gly Glu Arg Ala Gly Lys His Trp Gly Ile Ala
            260                 265                 270

Met Leu Thr Ile Phe Leu Leu Leu Phe Ser Gln Tyr Ala Arg Asn
        275                 280                 285

Val Lys Phe Pro Leu Pro Ile Tyr Lys Ser Lys Gly Trp Thr Ala
    290                 295                 300

Tyr Lys Leu Gln Leu Phe Lys Met Phe Pro Ile Ile Leu Ala Ile Leu
305                 310                 315                 320

Val Ser Trp Leu Leu Cys Phe Ile Phe Thr Val Asp Val Phe Pro
                325                 330                 335

Pro Asp Ser Thr Lys Tyr Gly Phe Tyr Ala Arg Thr Asp Ala Arg Gln
            340                 345                 350

Gly Val Leu Leu Val Ala Pro Trp Phe Lys Val Pro Tyr Pro Phe Gln
            355                 360                 365

Trp Gly Leu Pro Thr Val Ser Ala Ala Gly Val Ile Gly Met Leu Ser
        370                 375                 380

Ala Val Val Ala Ser Ile Ile Glu Ser Ile Gly Asp Tyr Tyr Ala Cys
385                 390                 395                 400

Ala Arg Leu Ser Cys Ala Pro Pro Pro Ile His Ala Ile Asn Arg
                405                 410                 415

Gly Ile Phe Val Glu Gly Leu Ser Cys Val Leu Asp Gly Ile Phe Gly
            420                 425                 430

Thr Gly Asn Gly Ser Thr Ser Ser Ser Pro Asn Ile Gly Val Leu Gly
        435                 440                 445

Ile Thr Lys Val Gly Ser Arg Arg Val Ile Gln Tyr Gly Ala Ala Ser
    450                 455                 460

Cys Cys Ala Leu Gly Met Ile Gly Lys Phe Ser Ala Leu Phe Ala Ser
465                 470                 475                 480

Leu Pro Asp Pro Val Leu Gly Ala Leu Phe Cys Thr Leu Phe Gly Met
                485                 490                 495

Ile Thr Ala Val Gly Leu Ser Asn Leu Gln Phe Ile Asp Leu Asn Ser
            500                 505                 510

Ser Arg Asn Leu Phe Val Leu Gly Phe Ser Ile Phe Phe Gly Leu Val
            515                 520                 525

Leu Pro Ser Tyr Leu Arg Gln Asn Pro Leu Val Thr Gly Ile Thr Gly
        530                 535                 540

Val Asp Gln Val Leu Asn Val Leu Leu Thr Thr Ala Met Phe Val Gly
545                 550                 555                 560

Gly Cys Val Ala Phe Ile Leu Asp Asn Thr Ile Pro Gly Thr Pro Glu
                565                 570                 575

Glu Arg Gly Ile Arg Lys Trp Lys Lys Gly Val Gly Lys Gly Cys Lys
            580                 585                 590

Ser Leu Asp Gly Met Glu Ser Tyr Asp Leu Pro Phe Gly Met Asn
        595                 600                 605

Val Ile Lys Lys Tyr Lys Cys Phe Ser Tyr Leu Pro Ile Ser Pro Thr
    610                 615                 620

Phe Ala Gly Tyr Thr Trp Lys Gly Leu Gly Lys Glu Arg Gln Cys Arg
625                 630                 635                 640
```

```
Ser Ser Asp Glu Asp Ser Gln Ala Thr Val
                645                 650

<210> SEQ ID NO 11
<211> LENGTH: 20
<212> TYPE: DNA
<213> ORGANISM: Artificial Sequence
<220> FEATURE:
<223> OTHER INFORMATION: Sense degenerate oligonucleotide primer based
      upon SVCT1 cDNA sequence coding for amino acid residues 339-346
<220> FEATURE:
<221> NAME/KEY: misc_feature
<222> LOCATION: (9)..(9)
<223> OTHER INFORMATION: n is A or C or G or T/U
<220> FEATURE:
<221> NAME/KEY: misc_feature
<222> LOCATION: (15)..(15)
<223> OTHER INFORMATION: n is A or C or G or T/U

<400> SEQUENCE: 11
athgartcna thggngayta                                            20

<210> SEQ ID NO 12
<211> LENGTH: 20
<212> TYPE: DNA
<213> ORGANISM: Artificial Sequence
<220> FEATURE:
<223> OTHER INFORMATION: antisense degenerate oligoncleotide primer
      based upon the SVCT1 cDNA sequence coding for amino acid residues
      468-475
<220> FEATURE:
<221> NAME/KEY: misc_feature
<222> LOCATION: (12)..(12)
<223> OTHER INFORMATION: n is A or C or G or T/U
<220> FEATURE:
<221> NAME/KEY: misc_feature
<222> LOCATION: (18)..(18)
<223> OTHER INFORMATION: n is A or C or G or T/U

<400> SEQUENCE: 12
ccraaraada tngaraancc                                            20

<210> SEQ ID NO 13
<211> LENGTH: 24
<212> TYPE: DNA
<213> ORGANISM: Homo sapiens

<400> SEQUENCE: 13
atgatgggta ttggtaagaa tacc                                       24

<210> SEQ ID NO 14
<211> LENGTH: 24
<212> TYPE: DNA
<213> ORGANISM: Homo sapiens

<400> SEQUENCE: 14
agcaaggaac tacagataca tgcc                                       24
```